(12) United States Patent
Seeberger et al.

(10) Patent No.: US 7,160,517 B2
(45) Date of Patent: Jan. 9, 2007

(54) APPARATUS AND METHODS FOR THE AUTOMATED SYNTHESIS OF OLIGOSACCHARIDES

(75) Inventors: Peter H. Seeberger, Cambridge, MA (US); Obadiah J. Plante, Beverly, MA (US)

(73) Assignee: Massachusetts Institute of Technolgy, Cambridge, MA (US)

(*) Notice: Subject to any disclaimer, the term of this patent is extended or adjusted under 35 U.S.C. 154(b) by 624 days.

(21) Appl. No.: 09/932,277

(22) Filed: Aug. 17, 2001

(65) Prior Publication Data

US 2002/0085964 A1    Jul. 4, 2002

Related U.S. Application Data

(60) Provisional application No. 60/254,233, filed on Dec. 8, 2000, provisional application No. 60/226,169, filed on Aug. 18, 2000.

(51) Int. Cl.
  B01J 8/00  (2006.01)
  C07H 3/06  (2006.01)
(52) U.S. Cl. ............ 422/131; 422/129; 422/211; 422/105; 536/123.1; 536/55.1
(58) Field of Classification Search ........... 422/131, 422/134, 138, 105, 109, 110, 129, 190, 198; 536/124, 55.1
  See application file for complete search history.

(56) References Cited

U.S. PATENT DOCUMENTS

| | | | | |
|---|---|---|---|---|
| 4,598,049 A | | 7/1986 | Zelinka et al. | 435/287 |
| 4,610,847 A | | 9/1986 | Hood et al. | 422/102 |
| 5,256,549 A | * | 10/1993 | Urdea et al. | 435/91.1 |
| 5,403,927 A | * | 4/1995 | Bendiak | 536/124 |
| 5,405,585 A | * | 4/1995 | Coassin | 422/100 |
| 5,462,748 A | | 10/1995 | Lloyd et al. | 424/484 |
| 5,466,608 A | | 11/1995 | Lapluye et al. | 436/86 |
| 5,635,612 A | * | 6/1997 | Kahne | 536/18.5 |
| 6,323,339 B1 | * | 11/2001 | Seeberger et al. | 536/124 |

FOREIGN PATENT DOCUMENTS

| | | |
|---|---|---|
| EP | 0 355 266 A2 | 2/1990 |
| WO | WO 9808799 A1 * | 3/1998 |
| WO | WO 98/57181 | 12/1998 |
| WO | WO 00/20428 | 4/2000 |

OTHER PUBLICATIONS

Seeberger et al. Solid-Phase Oligosaccharide Synthesis: Preparation of Complex Structures Using a Novel Linker and Differen Glycosylating Agents. Oct. 28, 1999. Organic Letters, vol. 1, No. 11, pp. 1811-1814.*

Plante et al. "Synthesis and Use of Glycosyl Phosphates as Glycosyl Donors". Organic Letters, 1999, vol. 1, No. 2, pp. 211-214. Published on the Web on May 29, 1999.*

(Continued)

*Primary Examiner*—Hien Tran
*Assistant Examiner*—Jennifer A. Leung
(74) *Attorney, Agent, or Firm*—Dana M. Gordon; Foley Hoag LLP

(57) ABSTRACT

One aspect of the present invention relates to an apparatus for the efficient synthesis of oligosaccharides on a solid support, e.g., formed by subunit addition to terminal subunits immobilized on solid-phase particles. In certain embodiments, the apparatus of the present invention is used in combinatorial methods, e.g., as described herein, of synthesizing oligosaccharides.

28 Claims, 22 Drawing Sheets

OTHER PUBLICATIONS

Osborn and Khan; "Recent Developments in Polymer Supported Synthesis of Oligosaccharides and Glycopeptides", Tetrahedron 55: 1807-1850, (1999).

St Hilaire and Meldal; "Glycopeptide and Oligosaccharide Libraries", Angew. Chem. Int. Ed. 39:1162-1179, (2000).

Wang and Hindsgaul; "Combinatorial Carbohydrate Chemistry", Glycoimmunology 2 :219-236, (1999).

International Search Report Completed on May 14, 2002 and Mailed on May 22, 2002.

* cited by examiner

Acceptor bound solid-phase carbohydrate synthesis

Automated Oligosaccharide Synthesis

Chemical Issues:

- Choice of Resin (Merrifield's, Argopore, Tentagel)
- Linker: 
- Glycosylation Protocol
- Deprotection Protocol
- Capping Cycle
- Cleavage Method
- Purification Technique Practical Issues:

- Scale (µmol-mmol)
- Cycle Development/Time
- Temperature Control Device

Automated Oligosaccharide Synthesis with Glycosyl Phosphates: Coupling Cycle

| | Reagent/Solvent | Equivalents | Temperature | Time |
|---|---|---|---|---|
| Coupling | Donor | 5 | -15°C | 15 min |
| | TMSOTf | 5 | | |
| Washing | $CH_2Cl_2$ | | | 5 min |
| | THF | | | |
| Coupling | Donor | 5 | -15°C | 15 min |
| | TMSOTf | 5 | | |
| Washing | $CH_2Cl_2$ | | | 5 min |
| | THF | | | |
| Deprotection | $N_2H_4$-HOAc | | 15°C | 30 min |
| Washing | Pyr./AcOH | | | 5 min |
| Deprotection | $N_2H_4$-HOAc | | 15°C | 30 min |
| Washing | Pyr./AcOH | | | 5 min |
| | | | Cycle Time per residue | 110 min |

FIG. 11

**Automated Oligomannoside Synthesis:
Coupling Cycles**

| | Reagent/Solvent | Equivalents | Time |
|---|---|---|---|
| Coupling | Donor<br>TMSOTf | 10<br>0.5 | 30 min |
| Washing | $CH_2Cl_2$<br>THF | | 5 min |
| Coupling | Donor<br>TMSOTf | 10<br>0.5 | 30 min |
| Washing | $CH_2Cl_2$<br>THF | | 5 min |
| Deprotection | NaOMe | | 30 min |
| Washing | $CH_2Cl_2$<br>THF | | 5 min |
| Deprotection | NaOMe | | 30 min |
| Washing | $CH_2Cl_2$<br>THF | | 5 min |

25 μmol Scale — Cycle Time per residue 140 min

FIG. 15

APPARATUS AND METHODS FOR THE AUTOMATED SYNTHESIS OF OLIGOSACCHARIDES

RELATED APPLICATIONS

This application claims the benefit of priority to U.S. Provisional Patent Application Ser. No. 60/226,169, filed Aug. 18, 2000, and U.S. Provisional Patent Application Ser. No. 60/254,233, filed Dec. 8, 2000, the contents of both of which are hereby incorporated by reference.

BACKGROUND OF THE INVENTION

Biopolymers, such as polypeptides and polynucleotides, are routinely synthesized by solid-phase methods in which polymer subunits are added stepwise to a growing polymer chain immobilized on a solid support. For polynucleotides and polypeptides, this general synthetic procedure can be carried out with commercially available synthesizers that construct the biopolymers with defined sequences in an automated or semi-automated fashion. However, commercially available synthesizers do not allow the efficient synthesis of oligosaccharides; typically, the yields of oligosaccharides synthesized using the commercially available apparatus are poor.

The glycosylation reaction is one of the most thoroughly studied transformations in organic chemistry. In the most general sense, a glycosylation is the formation of an acetal connecting two sugar units. The majority of glycosylating agents follow similar paths of reactivity. The anomeric substituent acts as a leaving group thereby generating an electrophilic intermediate. Reaction of this species with a nucleophile, typically a hydroxyl group, leads to the formation of a glycosidic linkage. This reaction may proceed via a number of intermediates depending on the nature of the leaving group, the activating reagent and the solvent employed.

Glycosyl trichloroacetimidates, thioglycosides, glycosyl sulfoxides, glycosyl halides, glycosyl phosphites, n-pentenyl glycosides and 1,2-anhydrosugars are among the most reliable glycosyl donors (See FIG. 1). Despite the wealth of glycosylating agents available, no single method has been distinguished as a universal donor. Contrary to peptide and oligonucleotide synthesis, the inherent differences in monosaccharide structures make it unlikely that a common donor will prevail. Rather, individual donors will see use in the construction of certain classes of glycosidic linkages.

Solid-Phase Chemical Synthesis

Solution-phase oligosaccharide synthesis remains a slow process due to the need for iterative coupling and deprotection steps with purification at each step along the way. To alleviate the need for repetitive purification events, solid-phase techniques have been developed. In solid-phase oligosaccharide synthesis there are two methods available (See FIGS. 2 and 3). The donor-bound method links the first sugar to the polymer through the non-reducing end of the monomer unit (FIG. 2). The polymer-bound sugar is then converted into a glycosyl donor and treated with an excess of acceptor and activator. Productive couplings lead to polymer bound disaccharide formation while decomposition products remain bound to the resin. Elongation of the oligosaccharide chain is accomplished by converting the newly added sugar unit into a glycosyl donor and reiteration of the above cycle. Since most donor species are highly reactive, there is a greater chance of forming polymer-bound side-products using the donor-bound method.

Alternatively, acceptor bound strategies have found considerable use in solid-phase oligosaccharide synthesis (FIG. 3). In this approach, the first sugar is attached to the polymer at the reducing end. Removal of a unique protecting group on the sugar affords a polymer-bound acceptor. The reactive glycosylating agent is delivered in solution and productive coupling leads to polymer-bound oligosaccharides while unwanted side-products caused by donor decomposition are washed away. Removal of a unique protecting group on the polymer-bound oligosaccharide reveals another hydroxyl group for elongation.

While the merits of the donor-bound method have been demonstrated by Danishefsky and co-workers, the most popular and generally applicable method of synthesizing oligosaccharides on a polymer support remains the acceptor-bound strategy. For a review, see: P. H. Seeberger, S. J. Danishefsky, *Acc. Chem. Res.*, 31 (1998), 685. The ability to use excess glycosylating agents in solution to drive reactions to completion has led to widespread use of this method. All of the above mentioned glycosylating agents have been utilized with the acceptor-bound method to varying degrees of success.

Increasingly, there is an interest in the automated synthesis of oligosaccharides. For example, it is often of interest, in examining structure-function relationships involving sugars, to generate a mixture of oligosaccharides having different residues at a particular position or varying in anomeric configuration at a glycosidic linkage. As another example, oligosaccharides having a desired activity, such as a high binding affinity to a given receptor or antibody, may be identified by (a) generating a large number of random-sequence oligosaccharides, and (b) screening these oligosaccharides to identify one or more oligosaccharides having the desired binding affinity.

Current apparatus for synthesizing oligosaccharides are limited in both the number and quantity of the oligosaccharides which can be synthesized. These limitations have restricted the availability of oligosaccharides, both for structure-function studies, and for selection methods.

SUMMARY OF THE INVENTION

The present invention is directed to apparatuses and methods for the automated solid-phase synthesis of oligosaccharides that can utilize a reaction vessel containing at least one insoluble resin bead, a donor vessel(s) containing a monosaccharide donor solution, an activator vessel(s) containing an activating reagent solution, a deblocking vessel(s) containing a deblocking reagent solution, a solvent vessel(s) containing a solvent solution, a solution transfer system capable of transferring the solutions while maintaining them under an inert gas pressure, and a computer for controlling the solution transfer system. The insoluble resin bead(s) can be comprised of an octenediol functionalized resin.

One aspect of the present invention relates to an apparatus for the efficient synthesis of oligosaccharides on a solid support, e.g., formed by subunit addition to terminal subunits immobilized on solid-phase particles. In certain embodiments, the apparatus of the present invention is used in combinatorial methods, e.g., as described herein, of synthesizing oligosaccharides.

In accordance with another aspect of the invention, the insoluble resin beads contained within the reaction vessel can have glycosyl acceptors tethered to the resin beads via organic linkers. The organic linker can be comprised of glycosyl phosphate.

In accordance with a further aspect of the invention, the oligosaccharide synthesizer can have a temperature control unit for regulating the temperature of the reaction vessel. The temperature control unit can be controlled by the same computer which controls the solution control system. In accordance with yet a further aspect of the invention, the reaction vessel can be a double-wall structure which forms two cavities, wherein the first cavity accommodates the synthesis of oligosaccharides and wherein the second cavity accommodates a coolant of the temperature control unit. The double-wall structure of the reaction vessel can be made of glass.

In accordance with another aspect of the invention, the donor vessel(s) can contains glycosyl trichloroacetimidate and/or a glycosyl phosphate solution.

In accordance with another aspect of the invention, the activator vessel can contain a Lewis acid, such as trimethylsilyl trifluoromethanesunfonate.

In accordance with a further aspect of the invention, the deblocking vessel can contain a solution of sodium methoxide in methanol.

In accordance with another aspect of the invention, the solvent vessel(s) can contain dichloromethane, methanol and/or THF.

In accordance with another aspect of the invention, the synthesizer can further include a blocking vessel(s) containing a blocking reagent solution. The blocking vessel(s) can contain, for example, benzyl trichloroacetimidate or a carboxylic acid.

In certain embodiments, the present invention relates to a method of forming a carbon-heteroatom bond between a glycosyl donor and a substrate, comprising the step of combining in solution, in the reaction vessel of an apparatus of the invention, a glycosyl donor comprising a reactive anomeric carbon, a substrate comprising a heteroatom bearing a hydrogen, and an activating reagent, wherein said activating reagent activates said reactive anomeric carbon of said glycosyl donor, thereby forming a product comprising a carbon-heteroatom bond between said anomeric carbon of said glycosyl donor and said heteroatom of said substrate. The glycosyl donor comprising a reactive anomeric carbon is selected from the group consisting of glycosyl phosphates, glycosyl phosphites, glycosyl trichloroacetimidates, glycosyl halides, glycosyl sulfides, glycosyl sulfoxides, n-pentenyl glycosides, and 1,2-anhydroglycosides. The heteroatom bearing a hydrogen of said substrate is selected from the group consisting of oxygen, nitrogen, and sulfur.

In certain embodiments of the method of the present invention, the activating reagent is a Lewis acid. In certain embodiments of the method of the present invention, the activating reagent is a silyl trifluoromethanesulfonate. In certain embodiments of the method of the present invention, the activating reagent is trimethylsilyl trifluoromethanesulfonate.

In certain embodiments of the method of the present invention, the substrate comprising a heteroatom bearing a hydrogen is tethered to a solid support via a covalent linker. In certain embodiments of the method of the present invention, said covalent linker is —O—(CH$_2$)$_3$CH=CH(CH$_2$)$_3$—O—. In certain embodiments of the method of the present invention, said solid support is a resin bead.

In certain embodiments of the method of the present invention, said glycosyl donor comprising a reactive anomenc carbon is tethered to a solid support via a covalent linker. In certain embodiments of the method of the present invention, said covalent linker is —O—(CH$_2$)$_3$CH=CH(CH$_2$)$_3$—O—. In certain embodiments of the method of the present invention, said solid support is a resin bead.

In certain embodiments of the method of the present invention, said substrate comprising a heteroatom bearing a hydrogen is selected from the group consisting of monosaccharides, oligosaccharides, polysaccharides, and glycoconjugates. In certain embodiments of the method of the present invention, said substrate comprising a heteroatom bearing a hydrogen is selected from the group consisting of monosaccharides, oligosaccharides, polysaccharides, and glycoconjugates.

In certain embodiments, a method of the present invention further comprises the steps of applying positive pressure or a vacuum to said reaction vessel of said apparatus, thereby removing the liquid phase from said reaction vessel of said apparatus; and adding solvent to said reaction vessel of said apparatus.

In certain embodiments, a method of the present invention further comprises the step of treating said product, in said reaction vessel of said apparatus, with a solution comprising a deprotection reagent, thereby removing from said product a protecting group to produce a second product comprising a heteroatom bearing a hydrogen, wherein said second product is tethered to a solid support via a covalent linker.

In certain embodiments, a method of the present invention further comprises the step of combining in solution, in said reaction vessel of said apparatus, a glycosyl donor comprising a reactive anomeric carbon, said second product comprising a heteroatom bearing a hydrogen, and an activating reagent, wherein said activating reagent activates said reactive anomeric carbon of said glycosyl donor, thereby forming a third product comprising a carbon-heteroatom bond between said anomeric carbon of said glycosyl donor and said heteroatom of said second product, wherein said third product is tethered to a solid support via a covalent linker.

In certain embodiments, a method of the present invention further comprises the step of treating said product, in said reaction vessel of said apparatus, with a solution comprising a converting reagent to produce a second product comprising a reactive anomeric carbon, wherein said second product is tethered to a solid support via a covalent linker.

In certain embodiments, a method of the present invention further comprises the step of combining in solution, in said reaction vessel of said apparatus, a substrate comprising a heteroatom bearing a hydrogen, said second product comprising a reactive anomeric carbon, and an activating reagent, wherein said activating reagent activates said reactive anomeric carbon of said second product, thereby forming a third product comprising a carbon-heteroatom bond between said anomeric carbon of said second product and said heteroatom of said substrate, wherein said third product is tethered to a solid support via a covalent linker.

BRIEF DESCRIPTION OF THE FIGURES

FIG. 11 depicts an overview of the steps in the automated synthesis of oligosaccharides using glycosyl phosphates.

FIG. 15 depicts an overview of the steps in the automated synthesis of oligomannosides.

DETAILED DESCRIPTION OF THE INVENTION

Definitions

Figure 1:
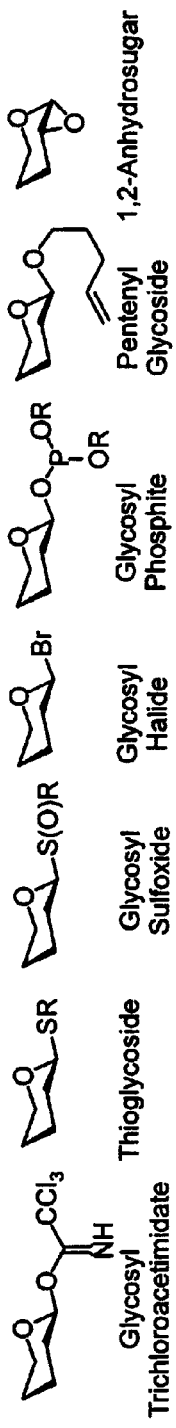
FIG. 1 depicts certain commonly used glycosylating agents.
Figure 2:
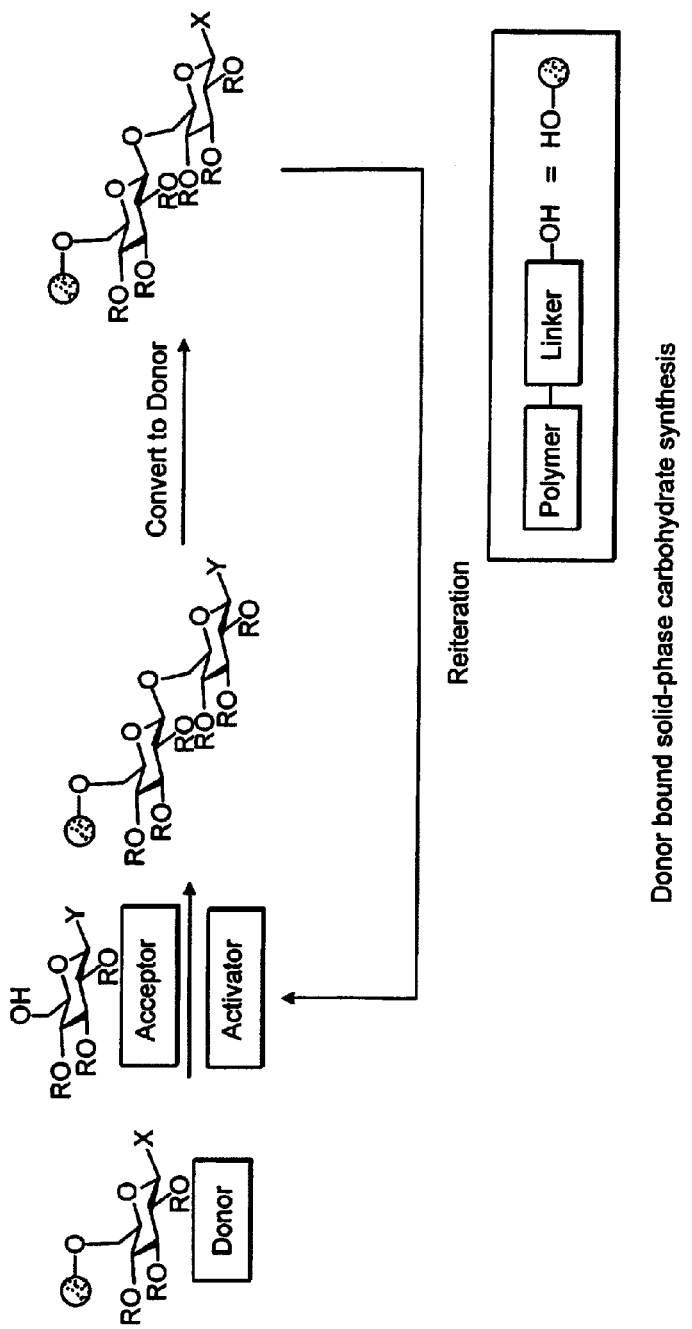
FIG. 2 generally depicts a donor bound solid-phase carbohydrate synthesis.
Figure 3:
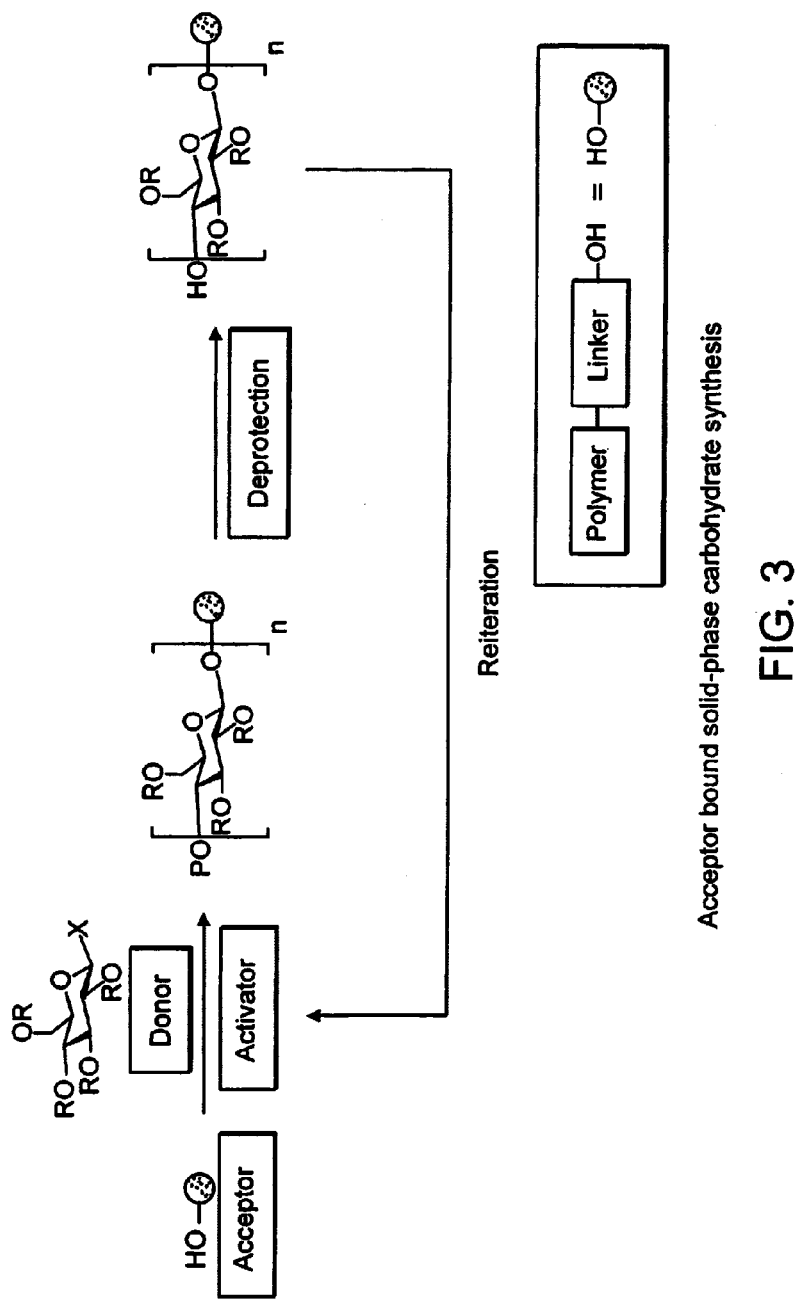
FIG. 3 generally depicts a acceptor bound solid-phase carbohydrate synthesis.

For convenience, certain terms employed in the specification, examples, and appended claims are collected here.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (σ) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), σ[P] indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

As used herein, the term "nitro" means —NO$_2$; the term "halogen" designates —F, —Cl, —Br or —I; the term "sulfhydryl" means —SH; the term "hydroxyl" means —OH; and the term "sulfonyl" means —SO$_2$—.

The terms "amine" and "amino" are art-recognized and refer to both unsubstituted and substituted amines, e.g., a moiety that can be represented by the general formula:

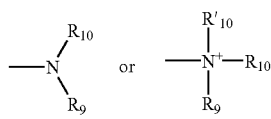

wherein $R_9$, $R_{10}$ and $R'_{10}$ each independently represent a group permitted by the rules of valence.

The term "acylamino" is art-recognized and refers to a moiety that can be represented by the general formula:

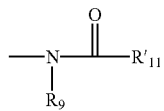

wherein $R_9$ is as defined above, and $R'_{11}$ represents a hydrogen, an alkyl, an alkenyl or —(CH$_2$)$_m$—R$_8$, where m and R$_8$ are as defined above.

The term "amido" is art recognized as an amino-substituted carbonyl and includes a moiety that can be represented by the general formula:

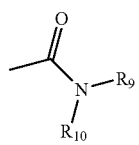

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

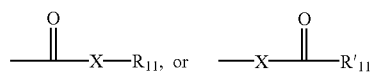

wherein X is a bond or represents an oxygen or a sulfur, and $R_{11}$ represents a hydrogen, an alkyl, an alkenyl, —(CH$_2$)$_m$—R$_8$ or a pharmaceutically acceptable salt, $R'^{11}$ represents a hydrogen, an alkyl, an alkenyl or —(CH$_2$)$_m$—R$_8$, where m and R$_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}$' is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The term "sulfonate" is art recognized and includes a moiety that can be represented by the general formula:

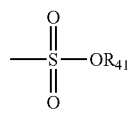

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The term "sulfate" is art recognized and includes a moiety that can be represented by the general formula:

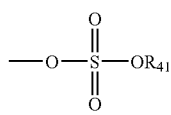

in which $R_{41}$ is as defined above.

The term "sulfonylamino" is art recognized and includes a moiety that can be represented by the general formula:

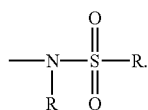

The term "sulfamoyl" is art-recognized and includes a moiety that can be represented by the general formula:

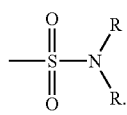

The term "sulfonyl", as used herein, refers to a moiety that can be represented by the general formula:

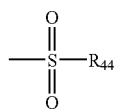

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

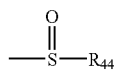

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as analgesics), wherein one or more simple variations of substituents are made which do not adversely affect the efficacy of the compound in binding to sigma receptors. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) *Trends Anal. Chem.* 14:83; the Affymax U.S. Pat. Nos. 5,359,115 and 5,362,899; the Ellman U.S. Pat. No. 5,288,514: the Still et al. PCT publication WO 94/08051; Chen et al. (1994) *JACS* 116: 2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A. Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of compounds can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequenceable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

Automation of Solid-Phase Oligosaccharide Synthesis

Access to defined sequences of peptides and nucleic acids by automated synthesis has had significant impact on research in a variety of areas involving these molecules. Important technologies such as PCR became possible after reliable access to short strands of DNA became routine. The field of glycobiology has suffered from the difficulties encountered in synthesizing complex oligosaccharides. Ideally, researchers interested in phenomena involving complex glycoconjugates could rely on automated synthesis to prepare the necessary molecules.

In one general application, the apparatus of the present invention is employed for generating oligosaccharides or mixtures thereof which can be used for structure-function analysis of oligosaccharides. For example, the oligosaccharide(s) of interest may be an antigenic oligosaccharide(s), an oligosaccharide(s) involved in protein-carbohydrate recognition events, or an antibiotic oligosaccharide(s). Typically, in structure-function studies, for example, it is desired to determine the effect on activity of one of a variety of sugar substitutions at one or more selected residue positions. In another general application, the apparatus is used to generate random-sequence oligosaccharides for selecting oligosaccharides with desired activity, typically binding activity to a known receptor, such as an antibody.

Figure 17:
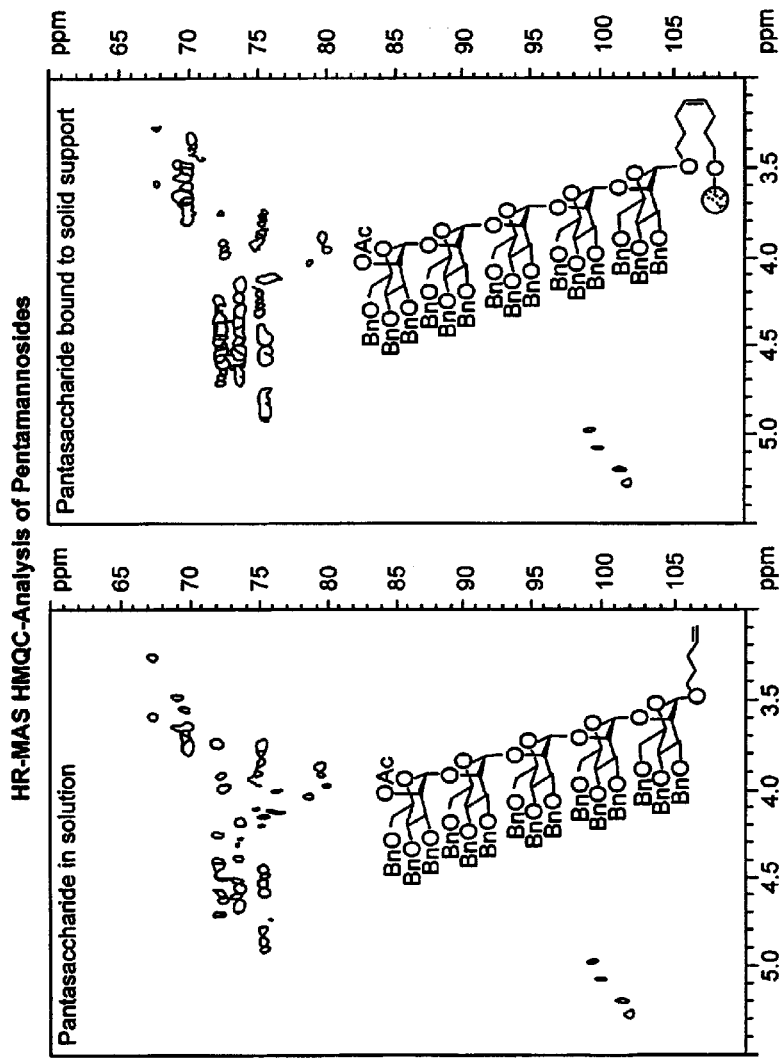
FIG. 17 depicts the HR-MAS HMQC data for an oligosaccharide, synthesized both using the apparatus of the present invention and in solution.
Figure 18:
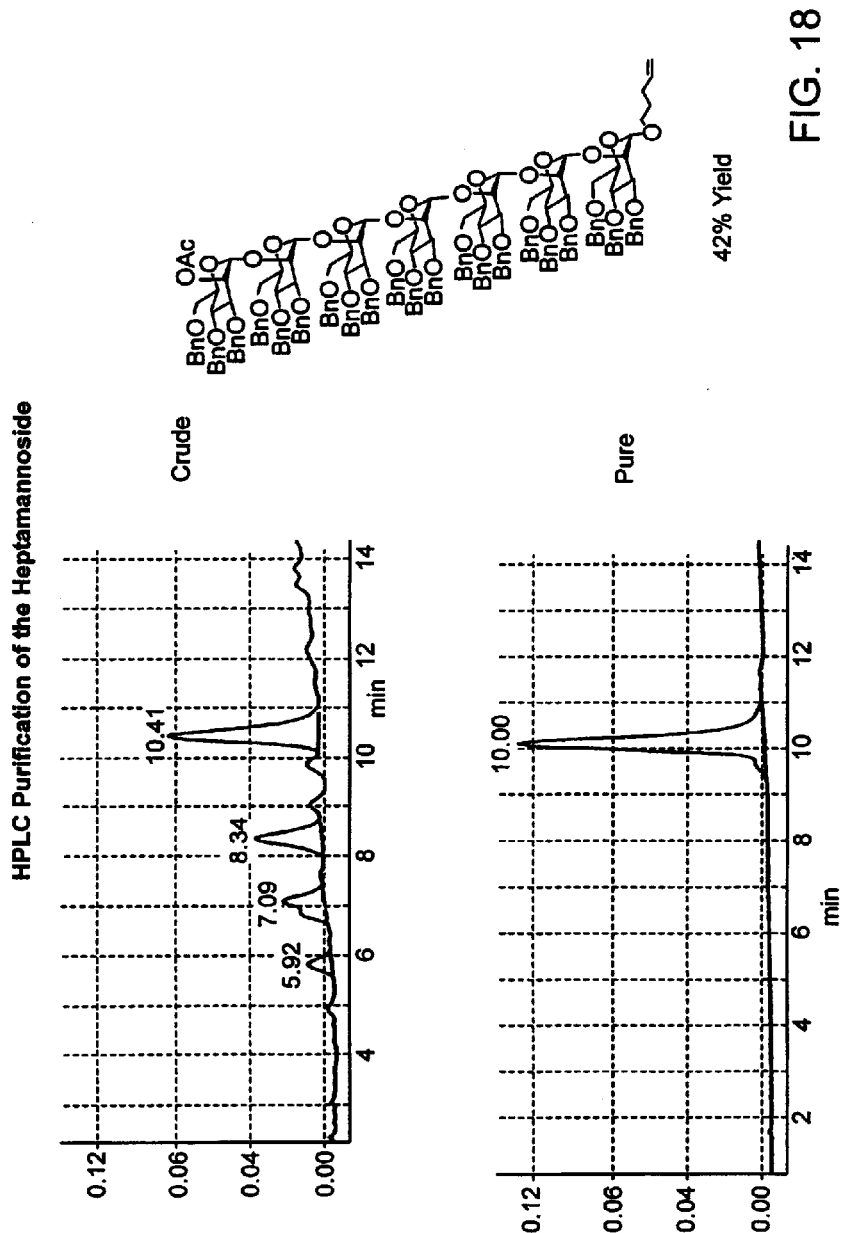
FIG. 18 depicts the HPLC data for a heptamannoside synthesized using the apparatus of the present invention.
Figure 19:
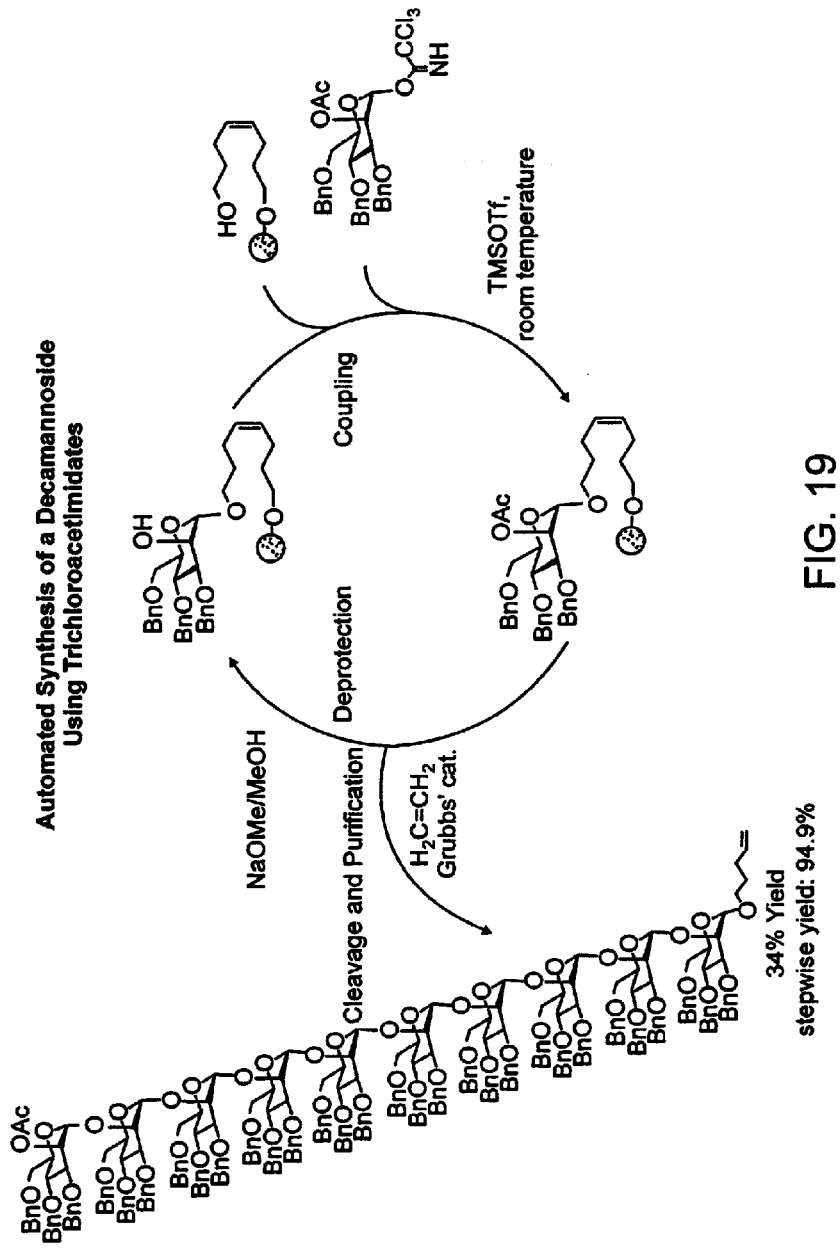
FIG. 19 depicts the automated synthesis of a decamannoside using trichloroacetimidate glycosyl donors.
Figure 20:
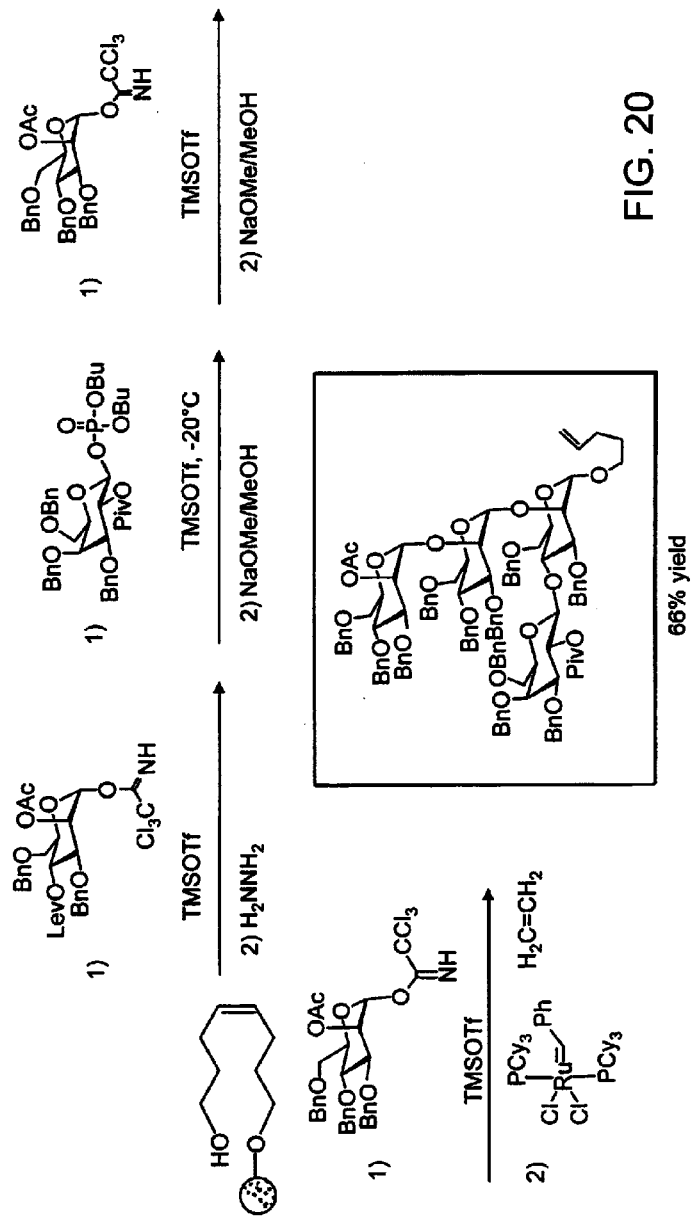
FIG. 20 depicts the automated synthesis of leishmania cap tetrasaccharide.
Figure 21:
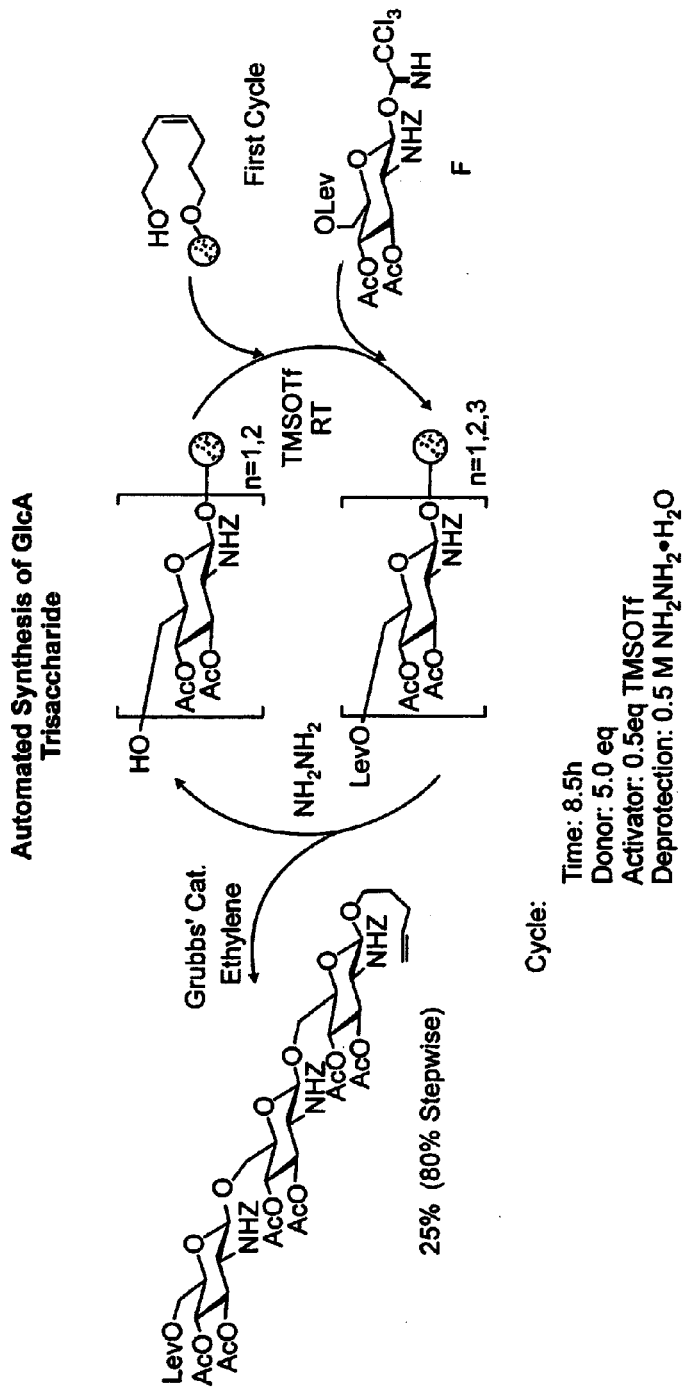
FIG. 21 depicts the automated synthesis of GlcA trisaccharide.
Figure 22:
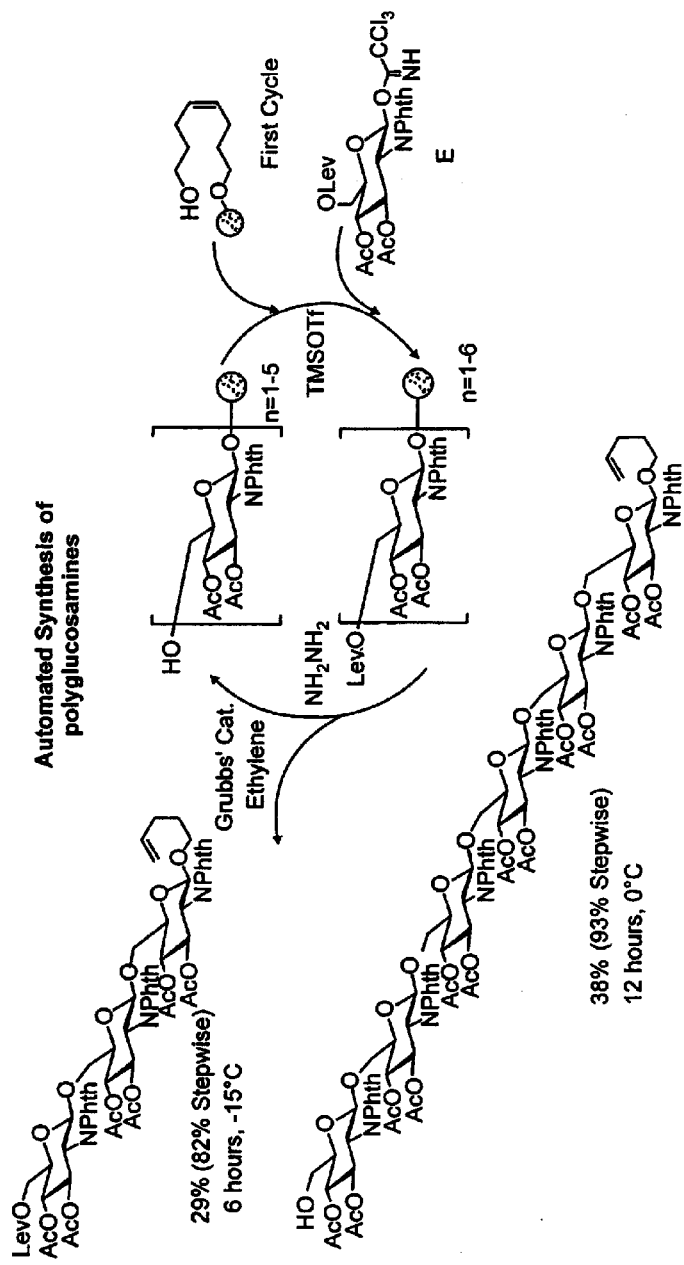
FIG. 22 depicts the automated synthesis of polyglucosamines.

While much progress in the development of solid-phase oligosaccharide synthesis has been achieved recently, no attempts at the automation of solid-phase oligosaccharide synthesis have been reported. Encouraged by the success of our attempts to synthesize oligosaccharides on solid support we began to carry out the assembly of carbohydrates in a synthesizer. We assembled a pentasaccharide in 8.5 hours in 75% overall yield in a fully automated fashion. An ABI 393B peptide synthesizer outfitted with a custom made reaction vessel was used to hold solutions of the mannose trichloroacetimidate donor, the activator (TMSOTf), and sodium methoxide in methanol as a deblocking solution. Methylene chloride, THF, and methanol were used as washing solvents while all reagents remained under an inert gas atmosphere. The coupling cycle was programmed to deliver five equivalents of donor and catalytic amounts of activator to the resin, followed by a 20 minute wait. After a washing step the glycosylation was repeated to ensure high yields. Following a rinse, a 20 minute deprotection revealed the next acceptor site. Repetition of this protocol fashioned the desired pentasaccharide in excellent stepwise coupling yields (>98%) and purity. The HMQC spectra of support-bound crude pentasaccharide prepared by fully automated synthesis in 500 minutes is compared to the solution HMQC spectrum of pure reference pentasaccharide n-pentenyl glycoside prepared in solution. See FIG. 17. Although the line-width of the HR-MAS spectrum is broadened due to the polymer, it provides very strong evidence that the desired product was observed as the major compound after 10 synthetic steps. We have begun to evaluate the use of other glycosyl donors in combination with different supports and shorter coupling protocols to assemble larger oligosaccharides of biological significance.

Protocols for the Automated Solid-Phase Synthesis of Oligosaccharides

Reactions on the solid support lend themselves particularly well to automation. In preliminary work, we have synthesized a trimannoside in 91% overall yield on a peptide synthesizer which was adapted for solvent and reagent delivery.

Solid-Phase Linkers

A critical element of any solid-phase synthesis strategy is the choice of an appropriate linker group connecting the first sugar to the solid-support (Table 1). For a review of linkers for solid-phase organic synthesis see: F. Guillier, D. Orain, M. Bradley, *Chem. Rev.*, 100 (2000), 2091. The linker must be inert to the glycosylation conditions as well as the deprotection conditions. Equally important is the need for a high yielding cleavage event at the conclusion of a synthesis. Several acid and base labile linkers, similar to those employed in peptide and oligonucleotide synthesis, have been modified for oligosaccharide synthesis.

TABLE 1

Linkers and cleavage methods for solid-phase oligosaccharide synthesis

| Linker | Cleavage Product | Cleavage Conditions |
|---|---|---|
| 1 | 5 | Fluoride ion |
| 2 | 6 | UV-radiation |
| 3 | 7 | NBS, ROH or $Hg^{++}$ |
| 4 | 8 | 9 |

Silyl ethers are most commonly used for monomer attachment to a polymer support under the donor-bound paradigm. Linkers such as diisopropyl phenylsilyl ether 1 are stable to mildly acidic and strongly basic reaction conditions and have proven valuable when glycosyl trichloroacetimidates, glycals, glycosyl fluorides and glycosyl sulfoxides are employed. Liberation from the polymer-support is accomplished upon treatment with fluoride sources, affording the free oligosaccharide unprotected at the original point of attachment. Due to the frequent use of silyl ethers as temporary protecting groups in oligosaccharide synthesis, the incorporation of a silyl linker often leads to significant challenges when differentiating the remaining hydroxyl groups.

A class of photolabile linkers has been developed to circumvent the use of silyl ethers as linkers and allow for the use of temporary silyl protecting groups. U. Zehavi, A. Patchornik, *J. Am. Chem. Soc.*, 95 (1973), 5673; R. Rodebaugh, B. Fraser-Reid, H. M. Geysen, *Tetrahedron Lett.*, 38 (1997), 7653. Photolabile linkers, such as 2, often involve the use of o-nitrobenzyl ether groups. This functional group is stable to a variety of conditions, however, cleavage from the polymer support is often slow and yields vary. Nonetheless, photolabile linkers offer another degree of orthogonality that is valuable when designing a synthesis.

A linker strategy that is unique to oligosaccharide synthesis involves the attachment of the first sugar to a polymer-support via a thioglycoside. As discussed above, thioglycosides are moderately stable to acid and inert under basic conditions. Thioglycosides, such as 3, are cleaved from the polymer-support upon addition of thiophilic reagents such as N-bromosuccinimide or $Hg(O_2CCF_3)_2$ in the presence of an alcohol or water to afford either acetal or hemiacetal products, respectively. The obvious limitations of this linker are the incompatibility with thioglycoside donors and the limited stability to treatment with acidic activators. Also, a mixture of anomers is possible and control of the anomeric ratio is difficult since the cleavage event occurs at the reducing end.

More recently, linkers similar to 4, making use of olefin metathesis as the cleavage method, have been developed. Olefinic linkers are stable to acidic and basic reaction conditions and the double bond acts as a handle for the final cleavage event. This option is attractive because the linker functionality is inert under commonly used coupling and deprotection conditions and the final cleavage step is compatible with numerous protecting groups. Importantly, the cleavage product contains an olefin, thereby allowing for additional functional group manipulations.

Analagous to solution-phase oligosaccharide synthesis, no single glycosylation method or linker strategy has distinguished itself among the variety of solid-phase techniques available. The abundance of linker strategies provides useful flexibility when planning a synthesis. It is anticipated that the development of novel linker and cleavage strategies will allow for the synthesis of increasingly complex carbohydrates using solid-phase methods.

Coupling Cycles

The solid-phase coupling conditions we have developed has been applied to the assembly of oligosaccharides in an automated fashion. Many glycosylation reactions can be carried out at room temperature and involve reagents that are completely soluble and stable to prolonged storage at room temperature. Initially, we employed glycosyl trichloroacetimidate donors as monosaccharide building blocks, since these units can be coupled at room temperature. Ester and silyl protecting groups were applied as temporary masking groups since their removal is high yielding and quick.

The heptamannoside we prepared served as the first test sequence for the coupling cycle. Since no monitoring was performed, complete coupling and deprotection have to be assured. In a typical coupling cycle five equivalents of the glycosyl donor and the activator TMSOTf were delivered to the resin. After one hour, the resin was rinsed, and the coupling step was repeated. After rinsing the resin and several washing steps, sodium methoxide in methanol was added to the resin and allowed to react for one hour. The next coupling cycle began after a further washing step. Following the completion of the synthesis, the resin was subjected to cross-metathesis with ethylene to remove the finished oligosaccharide in form of a n-pentenyl glycoside. The success of the automated synthesis was assessed by analytical HPLC, comparing the amount of product to the sum of side products (mainly deletion sequences).

Introduction of a Capping Step

Deletion sequences missing just one sugar unit (n-1) are the most difficult to separate from the desired product and arise from incomplete coupling steps during any coupling cycle of the sequence. The oligosaccharide chains that fail to couple during one cycle, may be successfully glycosylated during the following elongation steps. Therefore, a severe purification problem may exist at the end of the synthesis. To avoid the elongation of failure sequences, a capping step (i.e., a blocking step) can be included into the coupling cycle. After each completed coupling, a highly reactive blocking group can be used to cap any free hydroxyl acceptors. For example, benzyl trichloroacetimidate can be employed as a capping reagent (activated with TMSOTf) to yield benzyl ethers in positions that were not glycosylated and render them unreactive throughout the synthesis. Using this straightforward capping step, the purification of the finished oligosaccharide products is expected to be greatly simplified, since the presence of (n-1)-deletion sequences will be minimized.

Automated Solid Phase Synthesis of Oligosaccharides

Figure 4A:
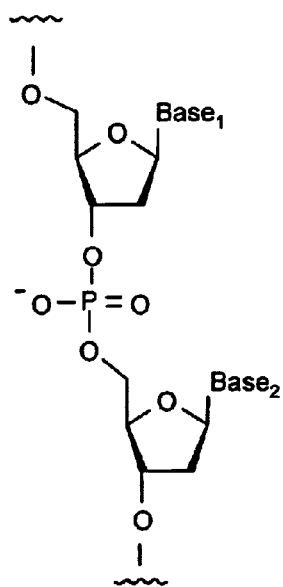
FIG. 4 depicts the major classes of repeating biooligomers responsible for signal transduction processes.
Figure 4B:
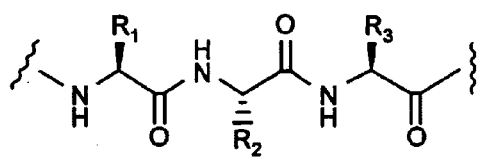
Figure 4C:
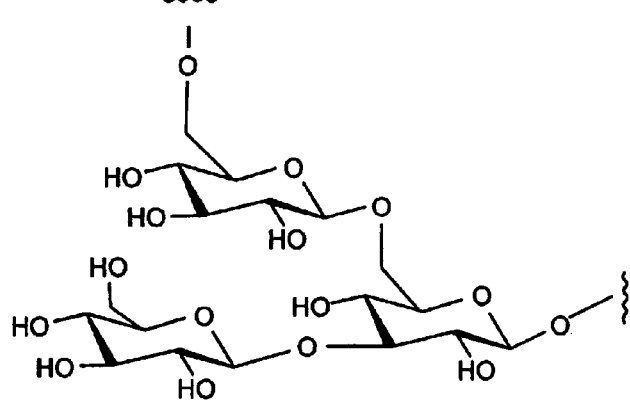

The transfer of information at the molecular level is a central process of life that in cellular systems relies mainly on the three major repeating biopolymers: proteins, nucleic acids, and carbohydrates (see FIG. 4). While the importance of proteins and nucleic acids in biology has been appreciated for a long time, the understanding of oligosaccharides and glycoconjugates in nature is still in its infancy. R. A. Dwek, Chem. Rev. 96, 683 (1996). Cell surface glycoconjugates are involved in signal transduction pathways and cellular recognition processes, and have been implicated in many disease states. S. Hakomori, Adv. Cancer Res. 52, 257 (1989).

A major impediment to the rapidly growing field of molecular glycobiology is the lack of pure, structurally defined carbohydrates and glycoconjugates. These biomolecules are often found in low concentrations and in microheterogeneous form in nature, greatly complicating their identification and isolation. The procurement of sufficient quantities of defined oligosaccharides required for detailed biophysical and biochemical studies therefore relies on efficient synthetic methods. While much progress has been made in oligosaccharide synthesis, the construction of complex carbohydrates remains time consuming and is carried out by a small number of specialized laboratories. G. J. Boons, Ed., Carbohydrate Chemistry (Blackie Publishers, London, 1998).

Historically, access to structurally defined complex carbohydrates has been very laborious. Recent advancements in solid phase synthesis have made the construction of complex oligosaccharides less tedious, however a high level of technical expertise is still necessary to obtain the desired structures. Here we describe the automated chemical synthesis of several oligosaccharides on a solid phase synthesizer. Through the use of glycosyl phosphate building blocks and a novel octenediol functionalized resin, a branched dodecasaccharide was synthesized. The target oligosaccharide was readily obtained after cleavage from the solid support. Access to complex oligosaccharides now has become feasible for even a non-expert, in a fashion much like the construction of oligopeptides and oligonucleotides.

Ultimately, a general, automated method for oligosaccharide assembly will allow even the non-specialist to rapidly prepare structures of interest. Oligonucleotides (M. H. Caruthers, Science 230, 281 (1985)) and oligopeptides (E. Atherton, R. C. Sheppard, Solid phase peptide synthesis: A practical approach, (Oxford University Press, Oxford, 1989)) are now routinely prepared in an efficient manner on automated synthesizers using solid phase strategies. The effect of an automated oligosaccharide synthesizer on the field of glycobiology may be readily envisioned when considering the significant impact peptide and nucleotide machines had on the biochemistry of these biopolymers.

Automated Oligosaccharide Synthesizer

We have developed the first automated solid phase oligosaccharide synthesizer. The solid phase paradigm lends itself particularly well to automation of the synthetic process. The repetitive nature of glycosylation and deprotection can easily be framed into a coupling cycle. Excess reagents are used to drive reactions to completion, while resin washes (through the use of solvents) remove any soluble impurities. Only a single purification step is necessary after the sugar is liberated from the solid support.

Mindful of the advantages of solid-support synthesis, we considered several key issues for the development of an automated oligosaccharide synthesizer: a) the design of an overall synthetic strategy with either the reducing or the non-reducing end of the growing carbohydrate chain attached to the support (see Y. Ito, S. Manabe, Curr. Opin. Chem. Biol. 2, 701 (1998)); b) selection of a polymer and linker that are inert to all reaction conditions during the synthesis but cleaved efficiently when desired; c) a protecting group strategy consistent with the complexity of the target oligosaccharide; d) stereospecific and high yielding glycosylation reactions; and e) an instrument capable of performing repetitive chemical manipulations at variable temperatures.

Furthermore, the moisture sensitivity of glycosylation reactions mandates a system that can be continuously maintained under an inert gas atmosphere. Additionally, since many glycosylation reactions require lower temperatures, a glass reaction vessel surrounded by a second cavity that allows for circulation of coolant can be used. The catalytic use of activators such as trimethylsilyl trifluoromethanesulfonate requires very precise measurements and deliveries of these reagents.

Rather than designing a new machine, we opted to reengineer an existing apparatus used in automated peptide synthesis. The Model 433A peptide synthesizer available from the Applied Biosystems Inc. was modified for our purposes. Several modifications were necessary before the commercially-available peptide synthesizer could be used for carbohydrate synthesis. The machine was equipped with several reagent bottles, some for washing and others for glycosylation and deprotection reagents. Small cartridges containing the donor species can be loaded into the synthesizer manually prior to the synthesis. A cycle was programmed to operate all steps without any operator intervention. The machine controlled the delivery of all reagents and donor species to the reaction vessel and the mixing of the contents of the vessel.

Figure 5:
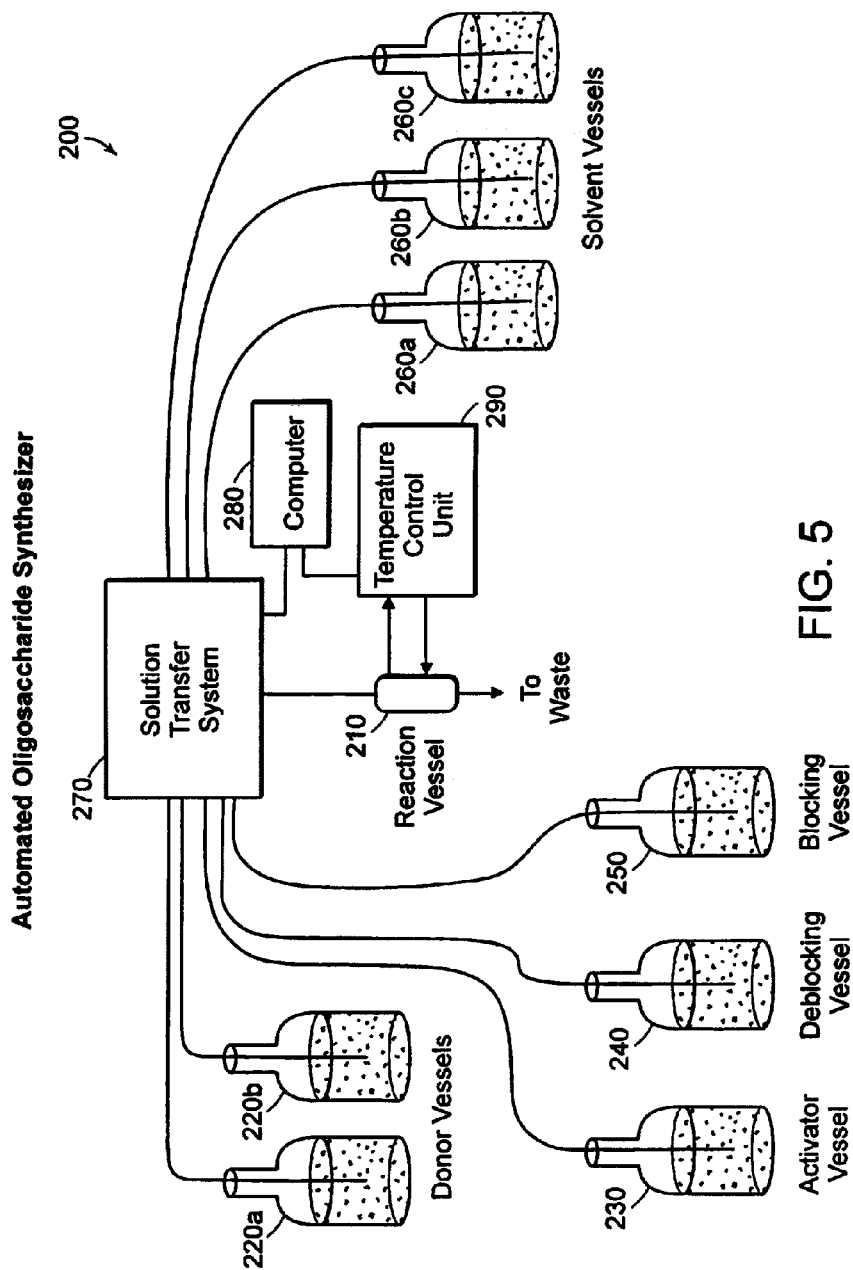
FIG. 5 depicts one embodiment of an automated oligosaccharide synthesizer in accordance with the present invention.

Referring now to FIG. 5, one embodiment of an automated oligosaccharide synthesizer 200 constructed in accordance with the invention is depicted. The automated oligosaccharide synthesizer 200 shown consists of a reaction vessel 210, two donor vessels 220a–b containing monosaccharide donor solutions, an activator vessel 230 containing an activating reagent solution, a deblocking vessel 240 containing a deblocking reagent solution, a blocking vessel 250 containing a blocking reagent solution, three solvent vessels 260a–c containing solvent solutions, a solution transfer system 270, a temperature control unit 290 for regulating the temperature of the reaction vessel 210 (i.e., maintaining the temperature of the reaction vessel 210 at a desired temperature(s)), and a computer 280 which can be preprogrammed to automatically control the solution transfer system 270 and the temperature control unit 290.

The donor vessels 220a–b can hold any suitable glycosyl donor solution, such as a glycosyl trichloroacetimidate or a glycosyl phosphate. The activator vessel 230 can hold any suitable activating reagent solution. Generally, Lewis acids have shown to be conductive to the formation, i.e., synthesis, of oligosaccharides and therefore can be utilized as an appropriate activator. Thus, the activator vessel 230 can contain a solution comprising a silyl trifluoromethanesulfonate or, alternatively, can contain a solution comprising trimethylsilyl trifluoromethanesulfonate. The deblocking vessel 240 can hold any suitable deblocking reagent solution, such as a solution containing sodium methoxide or hydrazine. The blocking vessel 250 can contain any suitable blocking reagent solution, such as a solution containing benzyl trichloroacetimidate or a carboxylic acid. One such suitable carboxylic acid is levulinic acid. The plurality of solvent vessels 260a–c can contain any suitable solvents solutions, such as dichloromethane, THF, and methanol, amongst others.

The solution transfer system 270 must be capable of transferring the donor, activating, deblocking, blocking and solvent solutions from their respective vessels to the reaction vessel 210. Due to the moisture sensitivity of certain glycosylation reactions, the solution transfer system 270 should also be capable of maintaining the reagents of the apparatus 200 under an inert gas atmosphere, i.e., maintain the reagents under positive pressure. Persons skilled in the art will appreciate that such solution transfer systems 270 are commercially and readily available; for example, the system of the Applied Biosystems Inc.'s Model 433A peptide synthesizer. The solution transfer system described in U.S. Pat. No. 5,186,898 is also a system which would be suitable for the synthesis of oligosaccharides in accordance with the present invention.

The computer 280 can be any suitable computing device for controlling the operations of the solution transfer system 270 and the temperature control unit 290, such as a personal computer or workstation, for example. The computer 280 can be preprogrammed so as to automatically control the operations of the solution transfer system 270; the coupling, washing, protecting/capping (i.e., blocking), and deprotecting cycles for a given protocol can be preprogrammed into the computer 280. In this way, the automated solid-phase synthesis of oligosaccharides can be controlled and achieved. Additionally, the computer 280 can be a device which is separate from the solution transfer system 270, or the computer 280 can be integral to the solution transfer system 270. If the computer 280 and the solution transfer system 270 are separate devices, then a suitable data communication path, such as a communication port/cable or IR data link, between the two devices must be present. Likewise, if automatic temperature control of the reaction vessel 210 is desired, then the computer 280 can be preprogrammed with the desired temperature protocol so as to control the operations of the temperature control unit 290. For the automatic control of the temperature control unit 290 via the computer 280, the computer 280 must be in data communication with the temperature control unit 290.

The temperature control unit 290 can be any suitable device which capable of regulating and maintain the temperature of the reaction vessel 210 at a desired temperature(s). Several of the external refrigerated circulators available from the Julabo USA, Inc., Allentown, Pa., can be used as an acceptable temperature control unit 290. To accomplish the automated solid-phase synthesis of many different types of oligosacchardis, the temperature control unit 290 should be capable of maintaining the temperate of the reaction vessel 210 at a set temperature of between −25 C and +40, and preferably at a set temperature of between −80 C and +60 C. The coolant of the temperature control unit 290 can be circulated around the reaction vessel 210 via a sleeve (not shown) which can surround the reaction vessel 210 and which is connected to the temperature control unit 290 via input and output pathways. Alternatively, the reaction vessel 210 can be a double-walled structure wherein the external cavity of the double-walled structure accommodates the coolant of the temperature control unit 290. The temperature of the reaction vessel 210 can be established by pre-programming the temperature control unit 290 to the desired temperature and then allowing the coolant to circulate around the reaction vessel 210 for some pre-established "cold soak" period, such as five minutes, for example. Alternatively, the temperature control unit 290 can have a temperature sensor placed on the wall of the reaction vessel 210 so as to obtain real-time temperature measurements of the actual reaction vessel 210 cavity, i.e., where the automated synthesis of the oligosaccharides are to take place. Thus, the temperature sensor can provide feedback data to the temperature control unit 290 so that the actual temperature of the reaction vessel 210 can more properly be maintained.

Figure 7:
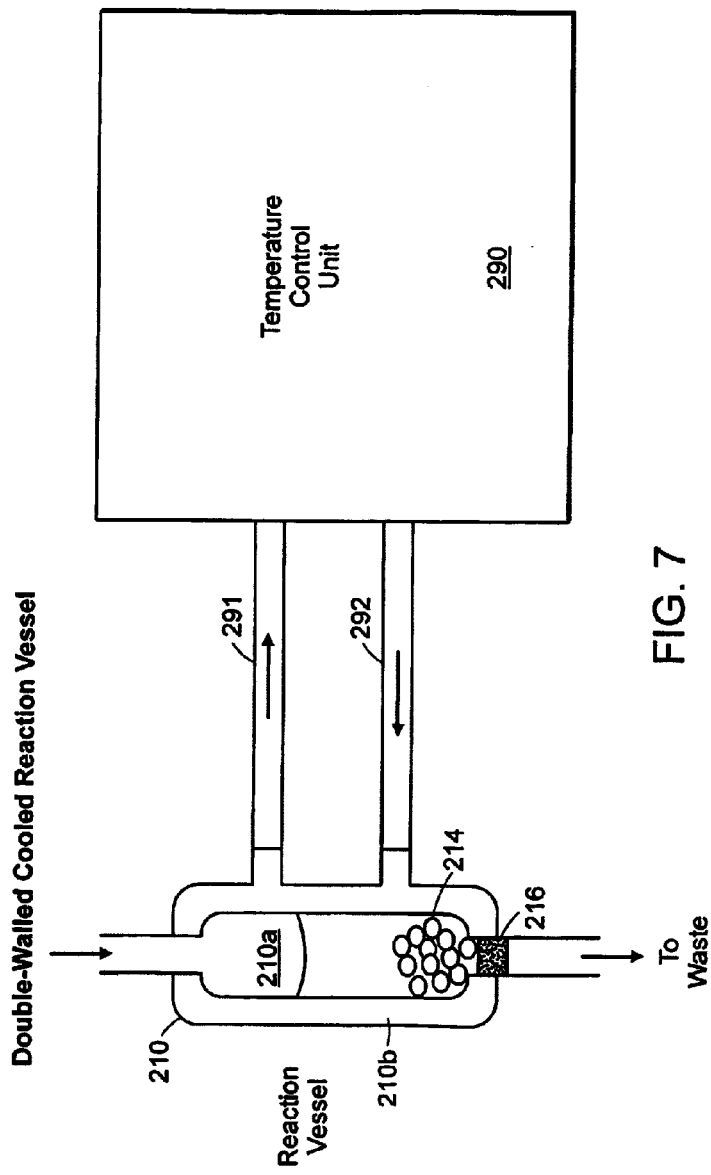
FIG. 7 depicts one embodiment of a double-walled cooled reaction vessel in accordance with the present invention.

Referring now to FIG. 7, one embodiment of a double-walled cooled reaction vessel 210 (shown in cross-sectional view) constructed in accordance with the invention is depicted. The double-wall structure of the reaction vessel 210 forms two cavities: first cavity 210a accommodates the synthesis of the oligosaccharides; second cavity 210b accommodates the coolant of the temperature control unit 290. The coolant of the temperature control unit 290 circulates through the second cavity 210b via conduits 291 and 292. These conduits 291 and 292 may be comprised of any suitable materials, such as rubberized materials or metallic materials, for example. Conduits 291 and 292 can be secured to the two opening found in the exterior surface of the double-walled reaction vessel 210 via mechanical clamping, tapes, bonds, epoxies etc. The double-walled cooled reaction vessel 210 can be made of glass or any other suitable material, such as titanium, for example.

The varies solutions are introduced into the cavity 210a via the solution transfer system 270 (FIG. 5). These solutions, likewise, can be forced out of cavity 210a (to be captured as waste)—through operation of the solution transfer system 270—by the introduction of additional solution or through the introduction of a compressed inert gas. Prior to the operation of the synthesizer apparatus, insoluble resin beads 214 can be placed into the cavity 210a of the reaction vessel 210. The resin beads 214 can be comprised of an octendiol functionalized resin and can further have a glycosyl acceptor tethered to the resin bead 214 via an organic linker (not shown). The organic linker can be comprised of a glycosyl phosphate. The solutions can exit the cavity 210a via a porous glass frit 216. The glass frit 216 allows the passage of the solutions but retains the resin beads 214 and, importantly, the oligosaccharides formed thereupon, within the cavity 210a of the reaction vessel 210.

Exemplification

The invention now being generally described, it will be more readily understood by reference to the following examples, which are included merely for purposes of illustration of certain aspects and embodiments of the present invention, and are not intended to limit the invention.

EXAMPLE 1

Automated Solid Phase Oligosaccharide Synthesis—General Experimental Procedures

General Methods

All chemicals used were reagent grade and used as supplied except where noted. Dichloromethane ($CH_2Cl_2$) used for washing cycles was purchased from Mallinckrodt (HPLC Grade) and used without further purification. Dichloromethane ($CH_2Cl_2$) used for reagent preparation was purchased from J.T. Baker (Cycletainer™) and passed through a neutral alumina column prior to use. Tetrahydrofuran (THF) was purchased from J.T. Baker (Cycletainer™) and passed through a neutral alumina column prior to use. Pyridine was refluxed over calcium hydride and distilled prior to use. Trimethylsilyl trifluoromethanesulfonate (TMSOTf) was purchased from Acros Chemicals. Sodium methoxide (25% w/v in MeOH), glacial acetic acid (AcOH) and hydrazine acetate (98%) were purchased from Aldrich Chemicals. Analytical thin-layer chromatography was performed on E. Merck silica gel 60 $F_{254}$ plates (0.25 mm). Compounds were visualized by dipping the plates in a cerium sulfate-ammonium molybdate solution followed by heating. Liquid column chromatography was performed using forced flow of the indicated solvent on Silicycle 230–400 mesh (60 Å pore diameter) silica gel. H NMR spectra were obtained on a Varian VXR-500 spectrometer (500 MHz) and are reported in parts per million (ppm) relative to $CHCl_3$ (7.27 ppm). Coupling constants (J) are reported in Hertz. C NMR spectra were obtained on a Varian VXR-500 spectrometer (125 MHz) and are reported in relative to $CDCl_3$ (77.23 ppm) as an internal reference. Polymer bound compounds were analyzed by HR-MAS NMR using the following conditions: All spectra were obtained on a Bruker DRX-600 spectrometer, operating at 600 MHz (H) equipped with a 4 mm Bruker CCA HR-MAS probe. Samples (10 mg at 0.45–0.55 mmol $g^{-1}$) were loaded into a ceramic rotor, suspended in 30–100 μL $CDCl_3$ and spun at the magic angle at 3.0 KHz. 1D-NMR analysis was perfomed using a 1D spin echo: 32 scans, 2 s relaxation time, 3 min total experiment time. TOCSY data was obtained using: mlevtp pulse sequence, 80 msec mixing time, 1 s relaxation delay, 16 scans per fid, 400 fids, 2048 points per fid, 2.2 h total experiment time. HMQC experiments were performed using: invbtp pulse sequence (HMQC with BIRD sequence), 1.3 s relaxation delay, 96 scans per fid, 256 fids, 2048 points per fid, 13.5 h total experiment time. MALDI-TOF mass spectrometry was performed on a PE Biosystems Voyager System 102 as follows: A 1 μl aliquot of matrix solution [10 mg/mL 2,5-dihydroxybenzoic acid (DHB) in THF] was spotted on the sample holder and allowed to dry. Addition of a 1 μl aliquot of oligosaccharide solution (5 mg/mL EtOAc) was co-spotted on the matrix, dried, and analyzed in the positive ion mode. HPLC analysis was performed on a Waters Model 600E Multisolvent delivery system using analytical (Nova-Pak® 60 Å, 4 μm, 3.6× 150 mm) and preparative Nova-Pak® 60 Å, 6 μm, 7.8×300 mm) silica columns.

General Procedure A. Automated Synthesis of α-(1→2)-mannosides:

Octenediol functionalized resin 1 (25 μmol, 83 mg, 0.30 mmol/g loading) was loaded into a reaction vessel and inserted into the oligosaccharide synthesizer. The resin was glycosylated using donor 2 (10 eq., 0.25 mmol, 160 mg) delivered in $CH_2Cl_2$ (4 mL) and TMSOTf (0.5 eq., 1 mL, 0.0125 M TMSOTf in $CH_2Cl_2$). Mixing of the suspension was perfomed (10 s vortex, 50 s rest) for 30 min. The resin was then washed with $CH_2Cl_2$ (6×4 mL each) and glycosylated a second time. Upon completion of the double glycosylation the resin was washed with: $CH_2Cl_2$ (6×4 mL each) and 1:9 MeOH:$CH_2Cl_2$ (4×4 mL each). Deprotection of the acetyl ester was carried out by treating the glycosylated resin with sodium methoxide (10 eq., 0.5 mL, 0.5 M NaOMe in MeOH) in $CH_2Cl_2$ (5 mL) for 30 min. The resin was then washed with and 1:9 MeOH:$CH_2Cl_2$ (1×4 mL) and subjected to the deprotection conditions a second time for 30 min. Removal of any soluble impurities was accomplished by washing the resin with: 1:9 MeOH:$CH_2Cl_2$ (4×4 mL each), 0.2 M AcOH in THF (4×4 mL each), THF (4×4 mL each), and $CH_2Cl_2$ (6×4 mL each). The deprotected polymer bound C2—OH α-mannoside was then elongated by reiteration of the above glycosylation/deprotection protocol. The terminal glycoside was not deprotected, thereby simplifying NMR analysis of the cleaved products.

General Procedure B. Oligosaccharide Cleavage from the Polymer Support:

The glycosylated resin (25 µmol) was dried in vacuo over phosphorous pentoxide for 12 h and transferred to a 10 mL flask. The flask was purged with ethylene and Grubbs' catalyst (bis(tricyclohexylphosphine)benzylidine ruthenium (IV) dichloride, 4.1 mg, 0.005 mmol, 20 mol %) was added. The reaction mixture was diluted with $CH_2Cl_2$ (3 mL) and stirred under 1 atm ethylene for 36 h. Triethylamine (111 mL, 0.80 mmol, 160 eq.) and tris hydroxymethylphosphine (50 mg, 0.40 mmol, 80 eq.) were added and the resulting solution was stirred at room temperature for 1 h. H. D. Maynard, R. H. Grubbs *Tetrahedron Lett.* 40, 4137 (1999). The pale yellow reaction mixture was diluted with $CH_2Cl_2$ (25 mL) and washed with water (3×25 mL), saturated aqueous $NaHCO_3$ (3×25 mL) and brine (3×25 mL). The aqueous phase was extracted with $CH_2Cl_2$ (3×25 mL) and the combined organics were dried over $Na_2SO_4$, filtered and concentrated. The resulting oligosaccharides were purified either by flash column chromatography on silica gel or high-pressure liquid chromatography (HPLC).

Pentamannoside 3.

Prepared by following general procedure A. The H-NMR spectrum of pentamer 3 was identical in all respects to an authentic sample previously synthesized. R. B. Andrade, O. J. Plante, L. G. Melean, P. H. Seeberger, *Org.Lett* 1, 1811 (1999). HR-MAS spectra of the resin bound pentamer were recorded using HMQC and TOCSY methods and are included below. All five characteristic anomeric proton resonances were observed in the HR-MAS TOCSY spectrum (4.8–5.5 ppm), including two anomeric protons that overlap in the IMQC spectrum.

Heptamannoside 4.

Prepared by following general procedure A. The spectral data of heptamer 4 was identical in all respects to an authentic sample previously synthesized. R. B. Andrade, O. J. Plante, L. G. Melean, P. H. Seeberger, *Org.Lett* 1, 1811 (1999). A H-NMR of pure 4 obtained from preparative HPLC purification of the heptamannoside synthesis is included below.

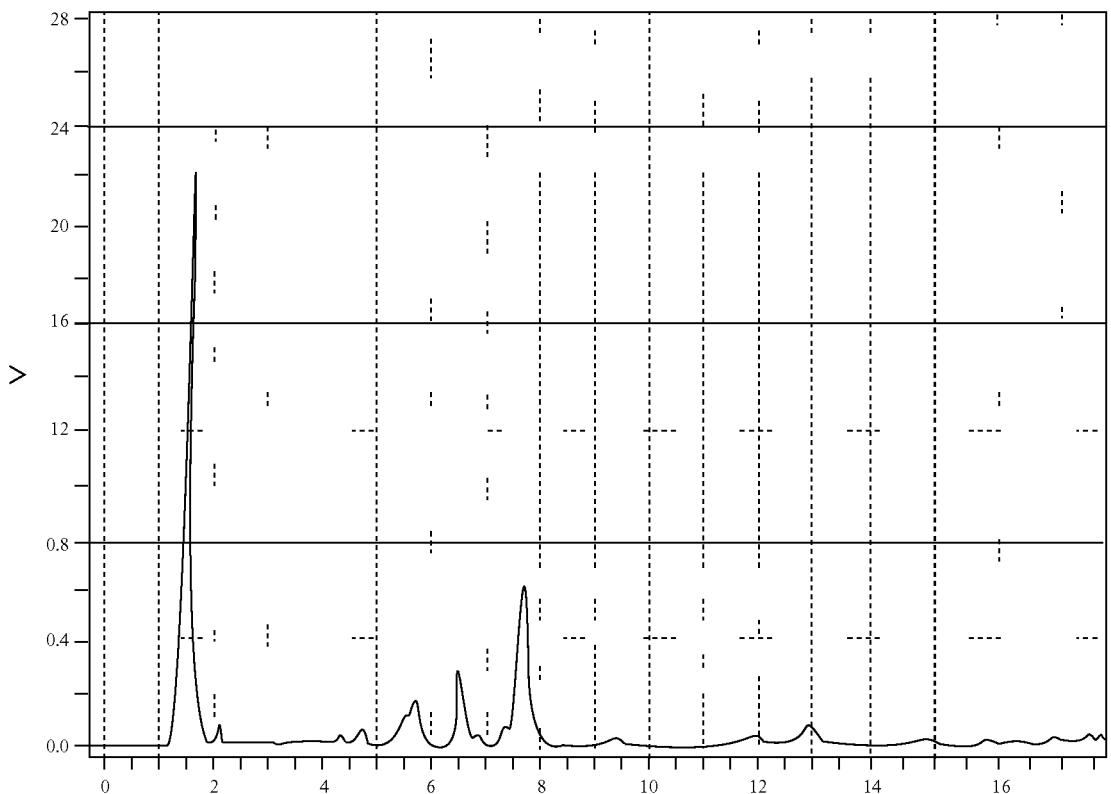

Analytical HPLC chromatogram of heptamannoside 4 synthesis following resin cleavage. Flow rate = 1 mL/min, 20 ⟶ 30% EtOAc/Hexanes (20 min): 7.8 min = heptamannoside 4, 6.2 min = hexamer, 5.4 min = pentamer.

Decamannoside 5.

Prepared by following general procedure A. The decamer was purified by preparative HPLC and characterized by H-NMR and MALDI-TOF. Characteristic anomeric resonances in the $^1$H-NMR spectrum (4.9–5.4 ppm) confirmed the decameric structure. A single acetate resonance (2.1 ppm) and n-pentenyl resonance (5.7 ppm) along with mass spectrometry data (calc. M$^+$+Na (4473.6), found MALDI-TOF (DHB, THF) M$^+$+Na (4474.0)) unambiguously identified decamer 5.

(4×4 mL each), THF (4×4 mL) and pyridine:acetic acid (3:2, 3×4 mL) and warmed to 15° C. Deprotection of the levulinoyl ester was carried out by treating the glycosylated resin with hydrazine acetate (40 eq., 4 mL, 0.25 M N$_2$H$_4$—HOAc in pyridine:acetic acid 3:2) for 15 min. The resin was subjected to the deprotection conditions a second time for 15 min. Removal of any soluble impurities was accomplished by washing the resin with: pyridine:acetic acid (3:2, 3×4 mL), 0.2 M AcOH in THF (4×4 mL each), THF (4×4 mL each), and CH$_2$Cl$_2$ (6×4 mL each). The deprotected polymer

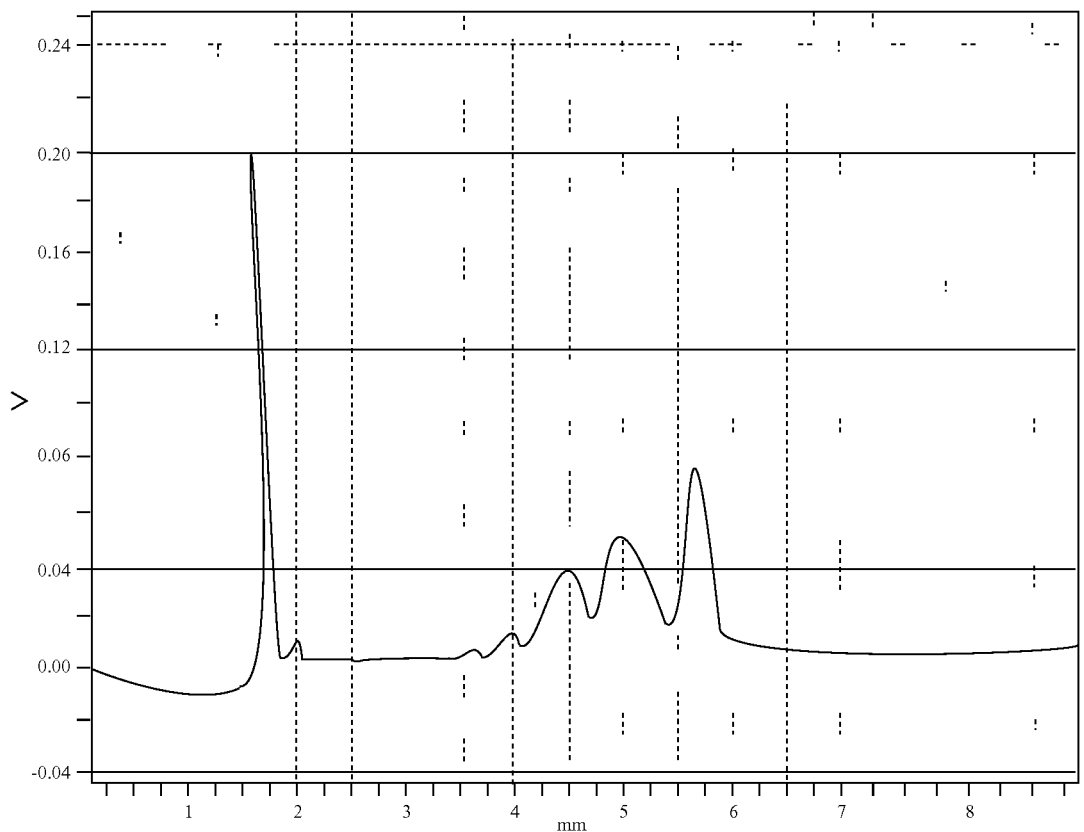

Analytical HPLC chromatogram of decamannoside 5 synthesis following resin cleavage. Flow rate = 1 mL/min, 20 ⟶ 25% EtOAc/Hexanes (20 min): 5.7 min = decamannoside 5, 5.0 min = nonamer, 4.4 min = octamer.

General Procedure C. Automated Synthesis of Phytoalexin Elicitor, β-glucan Oligosaccharides:

Octenediol functionalized resin 1 (25 µmol, 83 mg, 0.30 mmol/g loading) was loaded into a reaction vessel equipped with a cooling jacket and inserted into a modified ABI-433A peptide synthesizer. The resin was glycosylated using donor 8 or 9 (5 eq., 0.125 mmol, 90 mg and 146 mg respectively) delivered in CH$_2$Cl$_2$ (4 mL) and TMSOTf (5 eq., 1 mL, 0.125 M TMSOTf in CH$_2$Cl$_2$) at −15° C. Mixing of the suspension was perfomed (10 s vortex, 50 s rest) for 15 min. The resin was then washed with CH$_2$Cl$_2$ (6×4 mL each) and glycosylated a second time. Upon completion of the double glycosylation the resin was washed with: 1:9 MeOH:CH$_2$Cl$_2$ bound C6-OH β-glucoside was then elongated by reiteration of the above glycosylationldeprotection protocol using alternating donors 8 and 9. The terminal glycoside was not deprotected, thereby simplifying NMR analysis of the products liberated using general procedure B.

Phytoalexin Elicitor Hexasaccharide 10.

Prepared by following general procedure C. The hexamer was purified by preparative HPLC and characterized by $^1$H-NMR and MALDI-TOF. The characteristic t-butyl (1.2 ppm), n-pentenyl (5.7 ppm) and levulinoyl (2.2, 2.5, 2.7) resonances along with mass spectrometry data (calc. M$^+$+Na (2776.8), found MALDI-TOF (DHB, THF) M$^+$+Na (2778.0)) unambiguously identified hexamer 10.

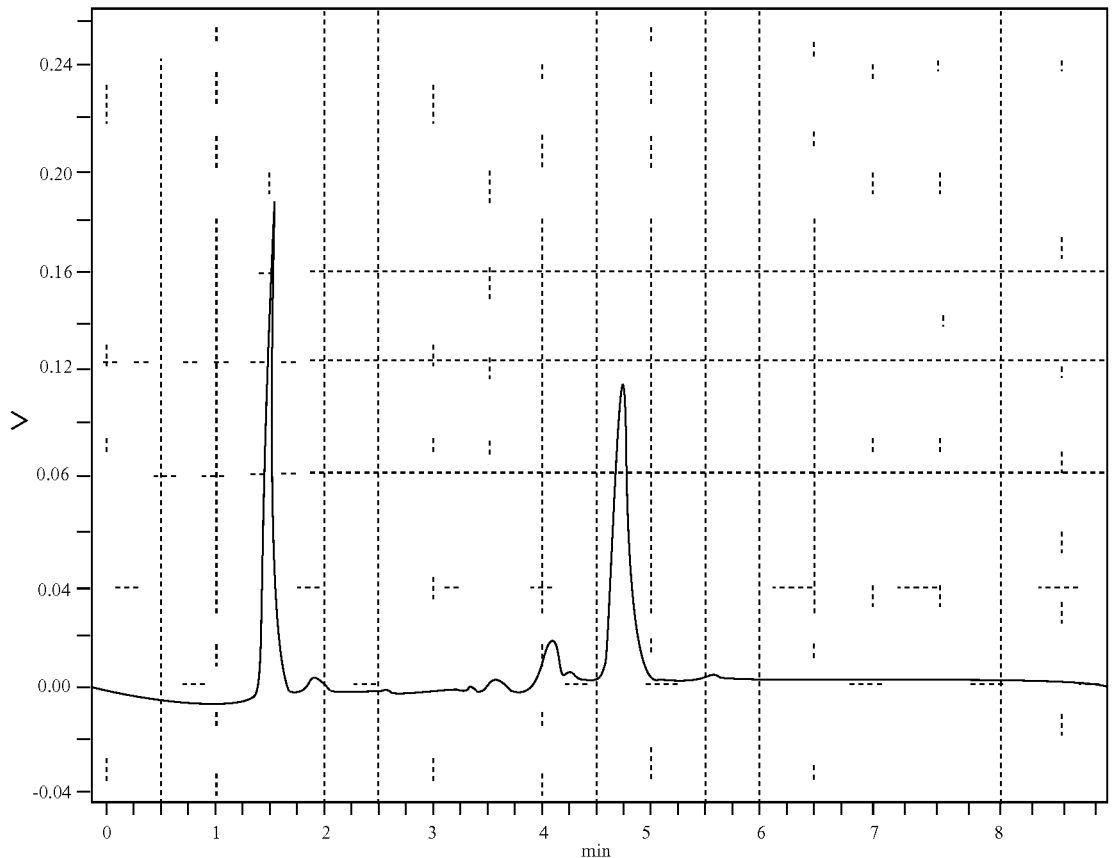

Analytical HPLC chromatogram of PE hexasaccharide 10 synthesis following resin cleavage. Flow rate = 1 mL/min, 17% EtOAc/Hexanes: 4.75 min = hexamer.

Phytoalexin Elicitor Dodecasaccharide 7.

Prepared by following general procedure C. The dodecamer was purified by preparative HPLC and characterized by $^1$H-NMR, $^{13}$C-NMR and MALDI-TOF. The characteristic t-butyl (1.2 ppm), n-pentenyl (5.7 ppm) and levulinoyl (2.2, 2.5, 2.7) resonances along with mass spectrometry data (calc. M$^+$+Na (5345.5), found MALDI-TOF (DHB, THF) M$^+$+Na (5346.2)) unambiguously identified dodecamer 7.

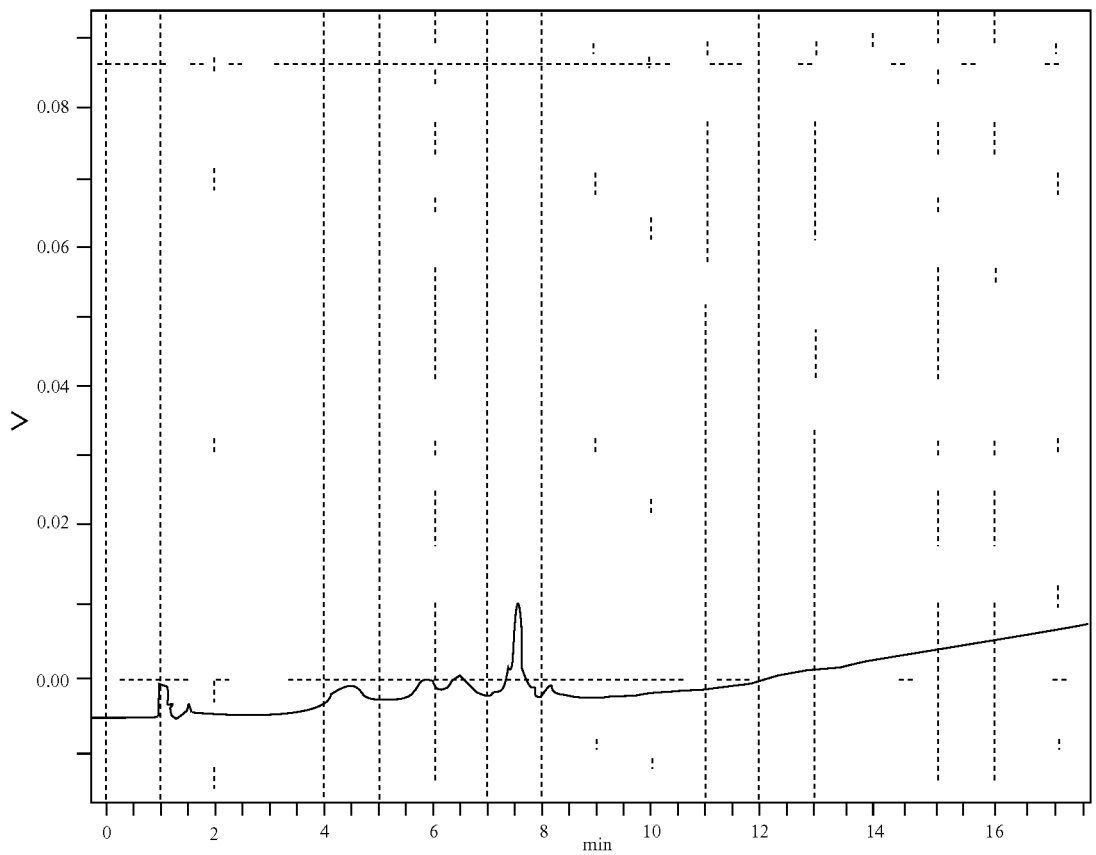

Analytical HPLC chromatogram of PE dodecasaccharide 7 synthesis following resin cleavage. Flow rate = 1 mL/min, 20 ⟶ 25% EtOAc/Hexanes: 6.7 min = dodecamer.

EXAMPLE 2

Using the modified peptide synthesizer, a systematic investigation of the variables involved in automated solid phase oligosaccharide synthesis was undertaken. We chose the "acceptor bound" strategy for solid phase oligosaccharide synthesis. B. Merrifield, *J. Am. Chem. Soc.* 85, 2149 (1963). In this method, the reactive glycosylating agent is delivered in solution while the nucleophilic acceptor hydroxyl group is exposed on the solid support. Productive coupling events result in support bound oligosaccharides that are purified by simply washing the soluble side products through a filter. Removal of a temporary protecting group on the newly formed saccharide unit reveals another hydroxyl group thereby continuing the coupling cycle.

The synthesis of biologically important α-mannosides has been the focus of significant research; therefore, these molecules (Scheme 1, 3–5) were chosen to establish an efficient automated cycle. Trichloroacetimidate donor 2 was chosen as the donor building block since it can be prepared on a multigram scale and activated at room temperature. See J. Rademann, R. R. Schmidt, *J. Org. Chem.* 62, 3989 (1997) and references therein. Activation of 2 was carried out under acidic conditions using the Lewis acid trimethylsilyl trifluoromethanesulfonate (TMSOTf). Removal of the acetyl ester protecting group was accomplished under basic conditions with sodium methoxide.

Scheme 1. Automated oligosaccharide synthesis using trichloroacetimidates

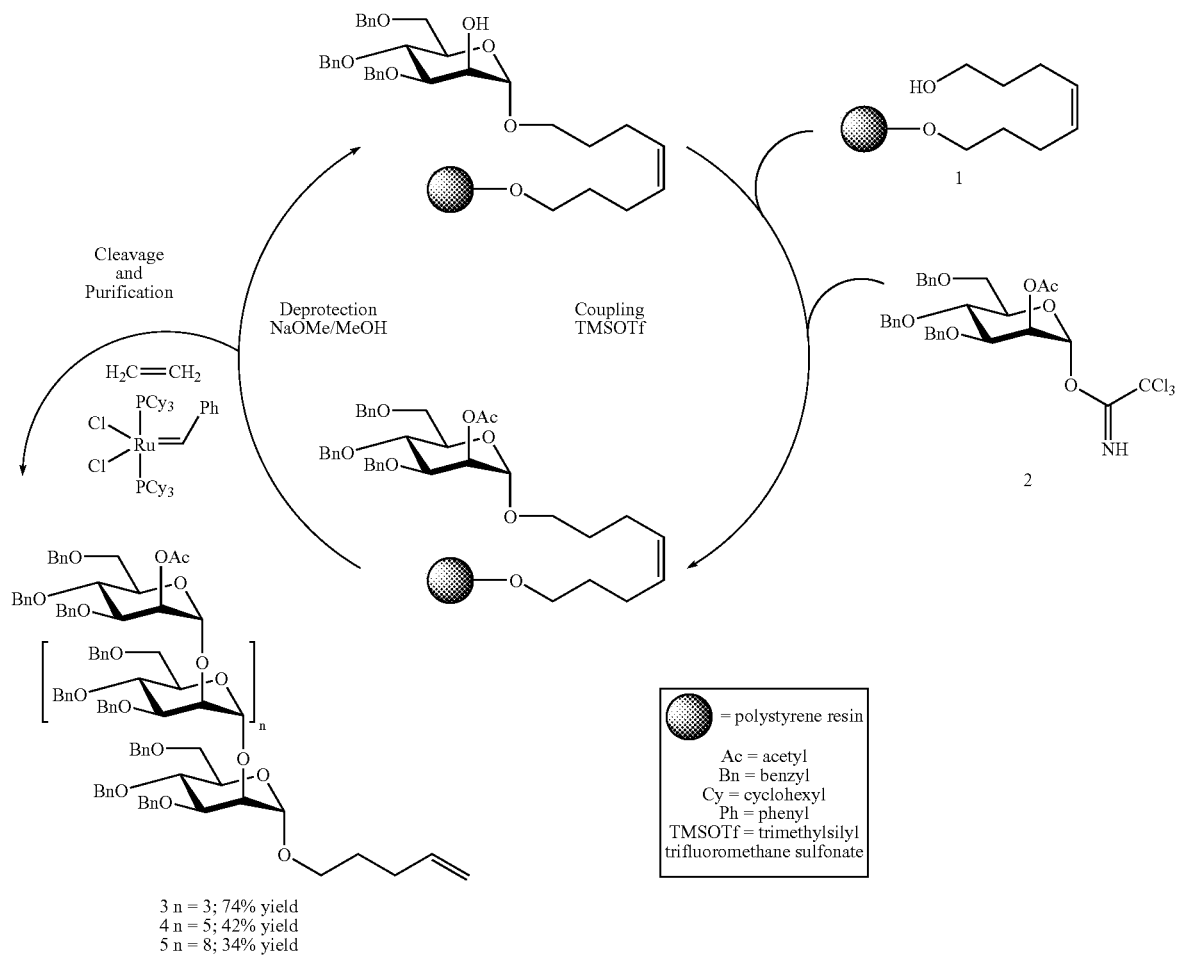

3 n = 3; 74% yield
4 n = 5; 42% yield
5 n = 8; 34% yield

Glycosylation Conditions: 25 μmol scale: 25 μmol resin (83 mg, 0.30 mmol/g loading); 10 Eq. Donor 2 (160 mg); 0.5 Eq. TMSOTf (1 mL, 0.0125 M TMSOTf in CH$_2$Cl$_2$) repeated two times for 30 min each. Deprotection Conditions: 25 μmol scale: 10 Eq. NaOMe (0.5 mL, 0.5 M NaOMe in MeOH) in 5 mL CH$_2$Cl$_2$ repeated teo times for 30 min each.

To allow for the use of acidic and basic reaction conditions in the coupling cycle, a polymer support and linker were investigated for compatibility. R. B. Andrade, O. J. Plante, L. G. Melean, P. H. Seeberger, Org.Lett 1, 1811 (1999). A variety of commercially available polymer supports were examined. Merrifield's resin (1% crosslinked polystyrene) and polystyrene based Argopre™ displayed excellent properties throughout the coupling cycle. Our previous work demonstrated that olefinic linker 1 was stable to the coupling cycle conditions while readily cleaved from the solid support at the end of the synthesis by olefin cross metathesis. By varying the concentration and quantity of reagents as well as the reaction times, we arrived at the cycle shown in Table 2. Applying the conditions in Table 2 with octenediol functionalized 1% crosslinked polystyrene, the synthesis of pentamannoside 3 was carried out in fourteen hours (Scheme 1).

TABLE 2

Cycle used with trichloroacetimidate donors (25 μmol scale)

| STEP | FUNCTION | REAGENT | Time (min) |
|---|---|---|---|
| 1 | Couple | 10 Eq. Donor and 0.5 Eq. TMSOTf | 30 |
| 2 | Wash | Dichloromethane | 6 |
| 3 | Couple | 10 Eq. Donor and 0.5 Eq. TMSOTf | 30 |
| 4 | Wash | Dichloromethane | 6 |
| 5 | Wash | 1:9 Methanol:Dichloromethane | 6 |
| 6 | Deprotection | 2 × 10 Eq. NaOMe (1:9 Methanol:Dichloromethane) | 80 |
| 7 | Wash | 1:9 Methanol:Dichloromethane | 4 |
| 8 | Wash | 0.2 M Acetic Acid in Tetrahydrofuran | 4 |
| 9 | Wash | Tetrahydrofuran | 6 |
| 10 | Wash | Dichloromethane | 6 |

Figure 8:
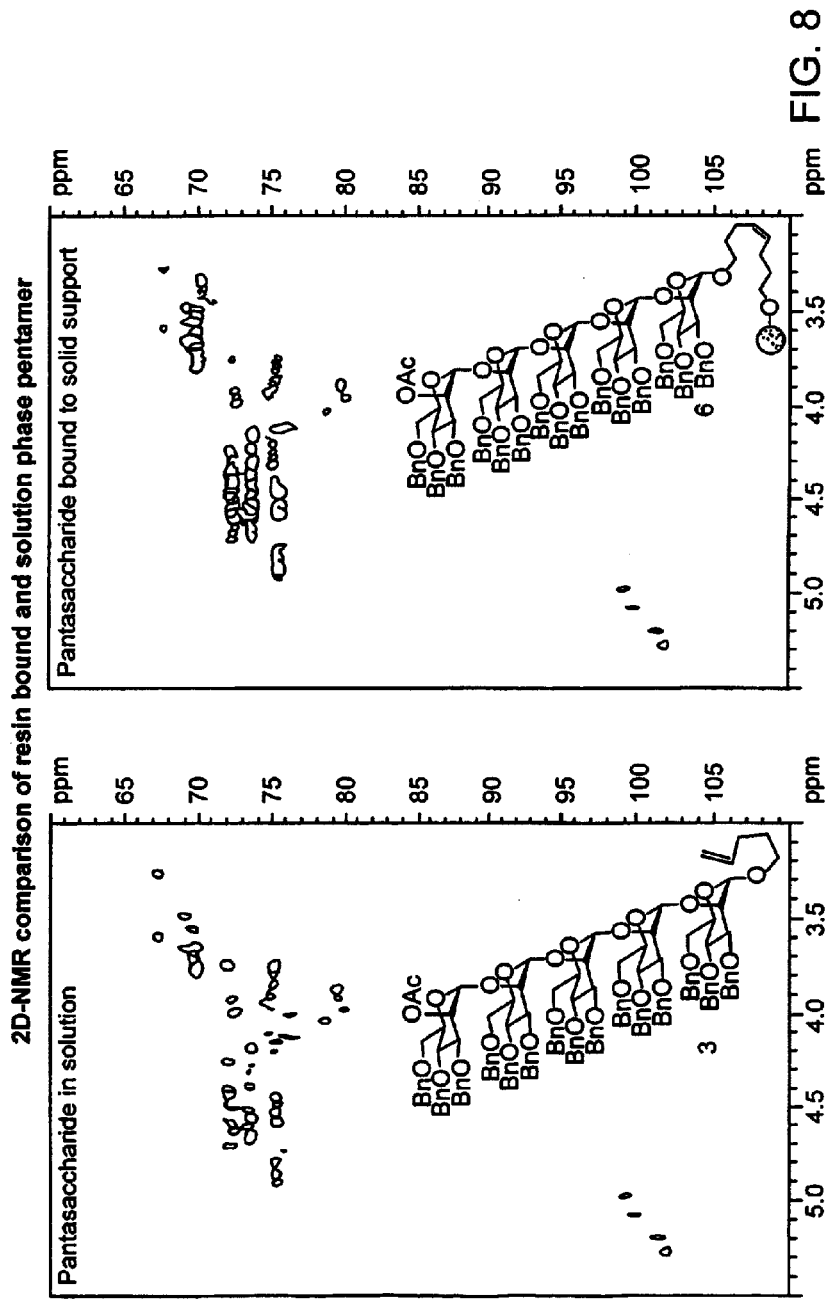
FIG. 8 presents a comparison of the 2D-NMR spectra of resin-bound and solution-phase pentasaccharides.

The ability to analyze the resin bound oligosaccharide is essential for the successful development of a solid phase synthesis method. B. Yan, *Acc. Chem. Res.* 31, 621 (1998). Two dimensional nuclear magnetic resonance analysis of the resin-bound pentamer 6 was performed using high-resolution magic angle spinning (HR-MAS NMR) techniques (see FIG. 8). Analysis of the NMR spectra revealed characteristic anomeric signals between 97 and 103 ppm. Further homonuclear TOCSY HR-MAS analysis confirmed the presence of five unique anomeric protons. For on-resin TOCSY analysis of 6 see the next Example. In accordance with previous experiments, minor line broadening was observed in the spectra of the resin bound sample. P. H. Seeberger, X. Beebe, G. D. Sukenick, S. Pochapsky, S. J. Danishefsky *Angew. Chem. Int. Ed. Engl.* 36, 491 (1997). Overall, the HR-MAS NMR data of the polymer bound pentamer corresponded unequivocally with an authentic pentamer sample prepared in solution. The remarkable purity of the resin-bound pentasaccharide 6, after nine synthetic steps without any purification, encouraged us to explore the synthesis of larger structures. Heptamer 4 and decamer 5 were prepared in average yields of 90–95% per step. The short reaction times, three hours per monomer unit, allowed for the synthesis of 4 in 20 hours and 42% overall yield. As a comparison, we manually synthesized heptamannoside 4 on the solid support in 14 days and 9% overall yield.

EXAMPLE 3

Figure 9:
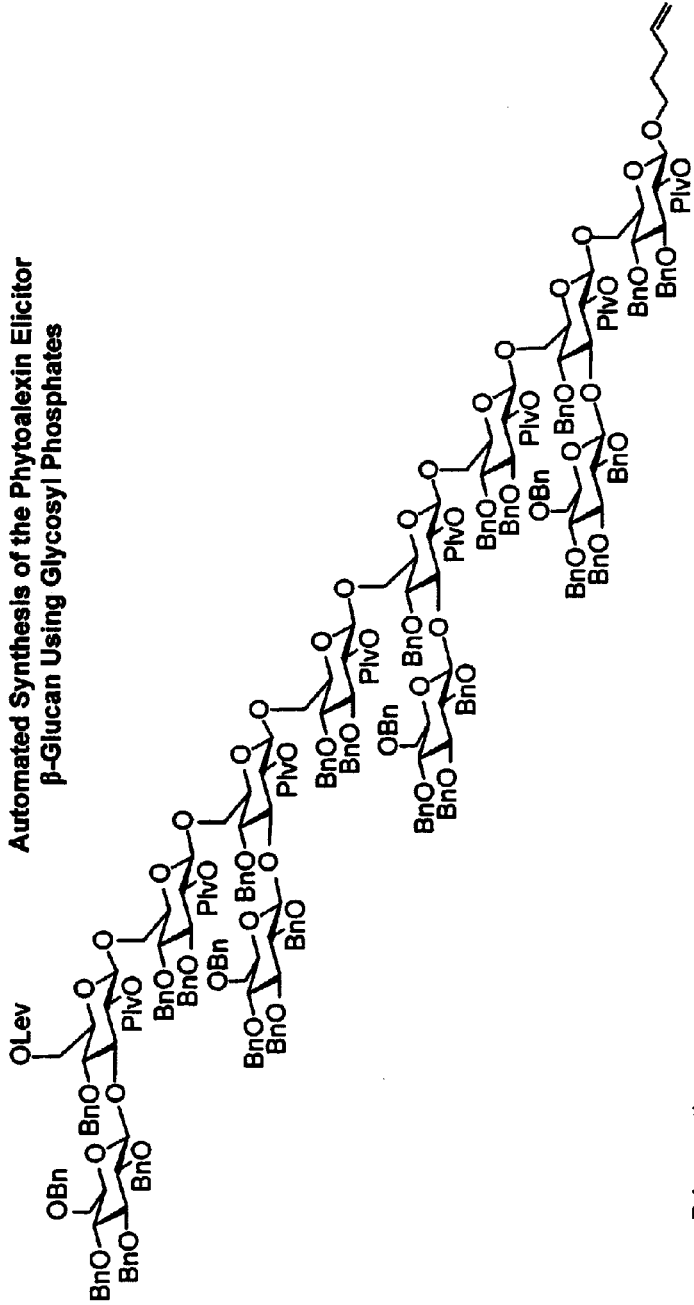
FIG. 9 depicts the fully protected phytoalexin elicitor (PE) β-glucan, synthesized using the apparatus of the present invention.
Figure 10:
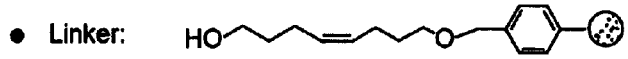
FIG. 10 depicts an overview of the automated solid phase synthesis of oligosaccharides.
Figure 12:
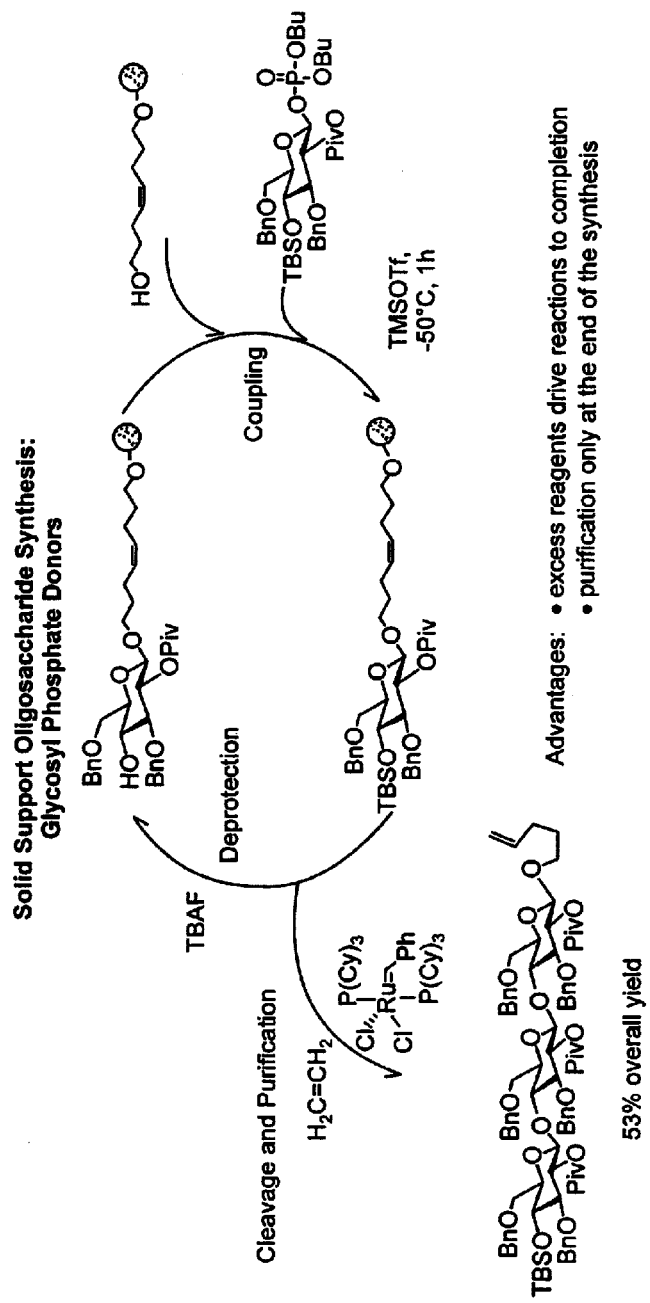
FIG. 12 depicts a cycle of oligosaccharide synthesis on the solid support using glycosyl phosphates.
Figure 13:
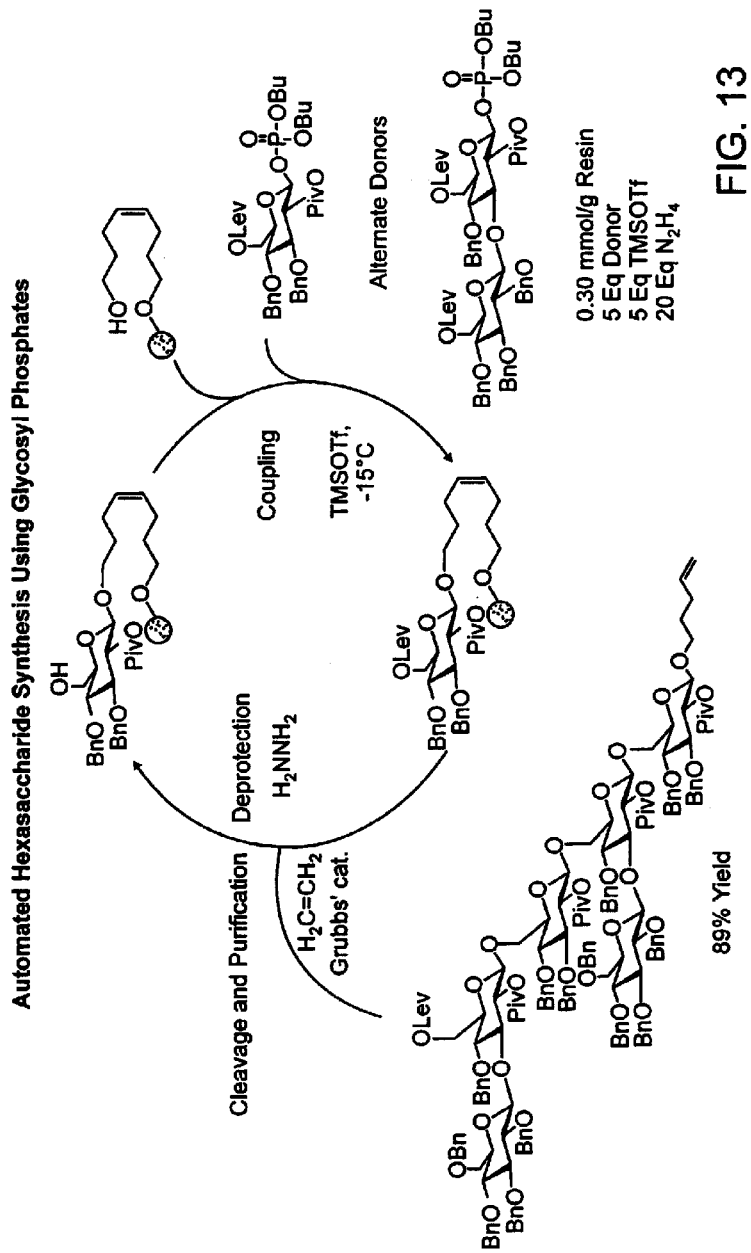
FIG. 13 depicts the automated synthesis cycle used in the synthesis of a hexasaccharide using glycosyl phosphates.
Figure 14:
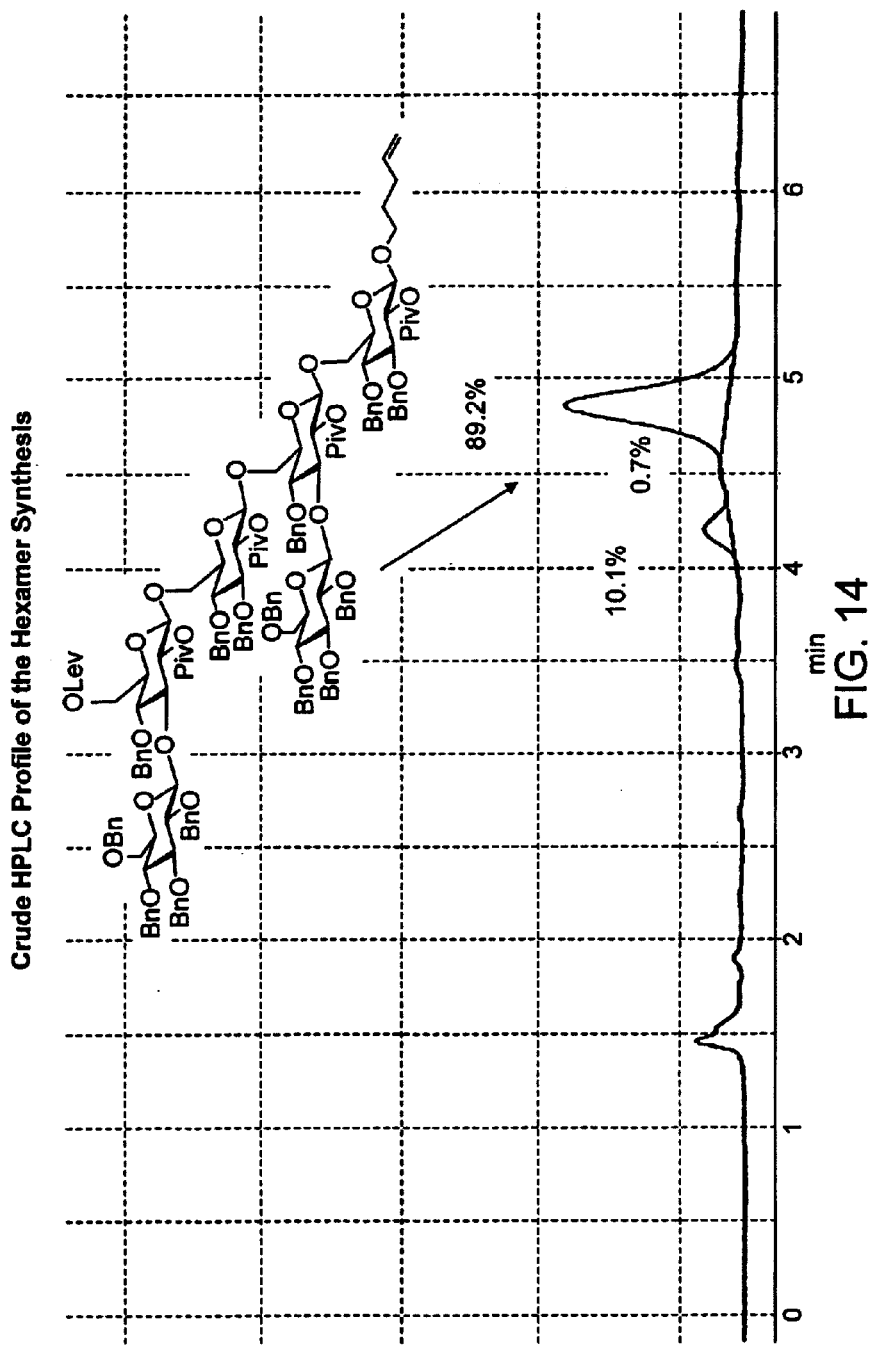
FIG. 14 depicts the HPLC data for a hexasaccharide synthesized using the apparatus of the present invention.
Figure 16:
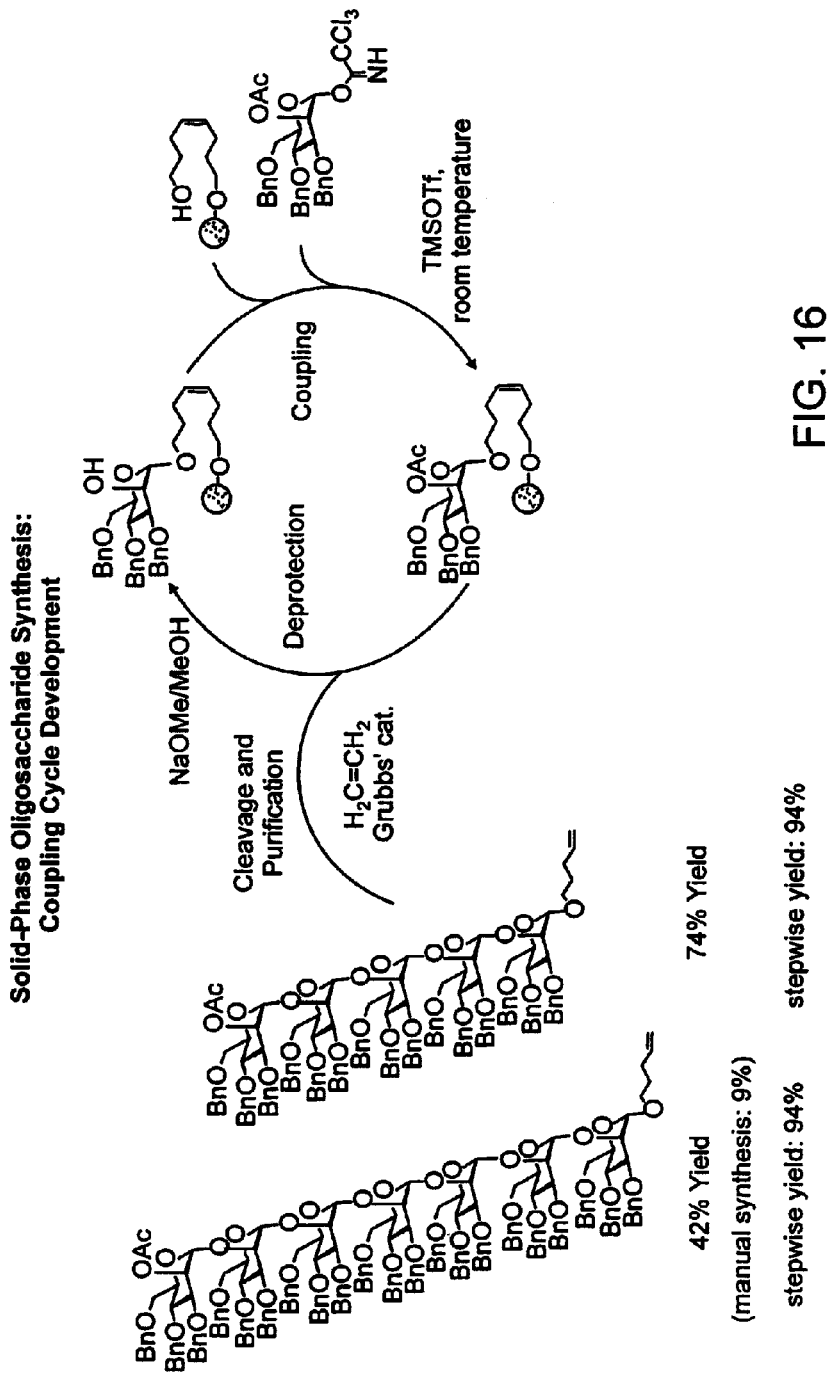
FIG. 16 depicts oligosaccharides synthesized using the methods and apparatus of the present, and the coupling cycle used to synthesize the oligisaccharides.

Given the success with the automated a-mannoside construction, the fully protected phytoalexin elicitor (PE) β-glucan 7 was selected as a more complex target structure (see FIG. 9). A. Darvill, et al., *Glycobiology* 2, 181 (1992). The presence of a fungal β-glucan oligosaccharide triggers the soybean plant to release antibiotic phytoalexins. The response initiated by the PE β-glucans in the host soybean plant is the most studied defense mechanism in plants. These oligosaccharides have been synthesized previously in solution and on the solid support and were expected to serve well as a benchmark in our automation endeavor. See P. Fugedi, W. Birberg, P. J. Garegg, Å. Pilotti, *Carb. Res.* 164, 297 (1987); and K. C. Nicolaou, N. Winsisinger, J. Pastor, F. DeRoose, *J. Am. Chem. Soc.* 119, 449 (1997) and references therein.

For the synthesis of the branched $\tilde{\beta}(1 \rightarrow 3)/\tilde{\beta}(1 \rightarrow 6)$ PE structure we envisioned the use of two different glycosyl phosphate donors, 8 and 9. Recently, we introduced glycosyl phosphates as valuable glycosylating agents that are readily prepared from glycal precursors. O. J. Plante, R. B. Andrade, P. H. Seeberger, *Org.Lett.* 1, 211 (1999). Strategic protecting group considerations prompted us to employ the levulinoyl ester as a 6-O temporary protecting group and the 2-O-pivaloyl group to ensure complete β-selectivity in the glycosylation reaction. Deprotection of the levulinoyl ester was accomplished with a hydrazine solution in pyridine/acetic acid while the phosphate building block was activated with TMSOTf.

Unlike peptide and nucleic acid synthesis, many of the manipulations involved in oligosaccharide chemistry are not carried out at room temperature. Drawing from solution phase studies, we were cognizant that the use of glycosyl phosphates, like many donors, would require low temperature for optimal results. D. Kahne, S. Walker, Y. Cheng, D. Van Enger, *J. Am. Chem. Soc.* 111, 6811 (1989). To address this need, we designed a temperature controlled reaction vessel. The vessel is enclosed by a cooling jacket that is easily attached to a commercial cooling apparatus. Model reactions with phosphate donor 8 demonstrated the ease of incorporating a temperature variable in the automation cycle.

The coupling and deprotection conditions were adjusted for the use of glycosyl phosphates and levulinoyl esters, resulting in the cycle shown in Table 3. The activation of phosphate donor 8 at –15° C. required shorter reaction times than were needed for trichloroacetimidate 2. The levulinate deprotection occurred at +15° C. and required only a fifteen minute reaction time, compared to the longer times commonly used for the acetyl ester cleavage. As in the synthesis of polymannosides 3–5, double glycosylations and double deprotections were employed. Incorporation of these modifications to the automated cycle resulted in an excellent yield and high purity of a model $\tilde{\beta}(1 \rightarrow 6)$ trisaccharide.

TABLE 3

Cycle used with phosphate donors (25 μmol scale)

| STEP | FUNCTION | REAGENT | Time (min) |
|---|---|---|---|
| 1 | Couple | 5 Eq. Donor and 5 Eq. TMSOTf | 15 |
| 2 | Wash | Dichloromethane | 6 |
| 3 | Couple | 5 Eq. Donor and 5 Eq. TMSOTf | 15 |
| 4 | Wash | 1:9 Methanol:Dichloromethane | 4 |
| 5 | Wash | Tetrahydrofuran | 4 |
| 6 | Wash | 3:2 Pyridine:Acetic Acid | 3 |
| 7 | Deprotection | 2 × 20 Eq. Hydrazine (3:2 Pyridine:Acetic Acid) | 30 |
| 8 | Wash | 3:2 Pyridine:Acetic Acid | 3 |
| 9 | Wash | 1:9 Methanol:Dichloromethane | 4 |
| 10 | Wash | 0.2 M Acetic Acid in Tetrahydrofuran | 4 |
| 11 | Wash | Tetrahydrofuran | 4 |
| 12 | Wash | Dichloromethane | 6 |

The automated cycle in Table 3 was then applied to the synthesis of more complex PE oligosaccharides, using alternating phosphate building blocks (Scheme 2). Branched hexasaccharide 10 was constructed in ten hours in over 80% yield as judged by HPLC analysis. Also, we prepared dodecasaccharide 7 in 17 hours and over 50% yield using the same cycle. Notably, the solution phase synthesis of only two phosphate building blocks was necessary, greatly reducing the manual labor usually required to assemble a structure of this size. The expedient generation of material via automation represents a major improvement over previous methods for polysaccharide synthesis.

Scheme 2. Automated oligosaccharide synthesis using glycosyl phosphates

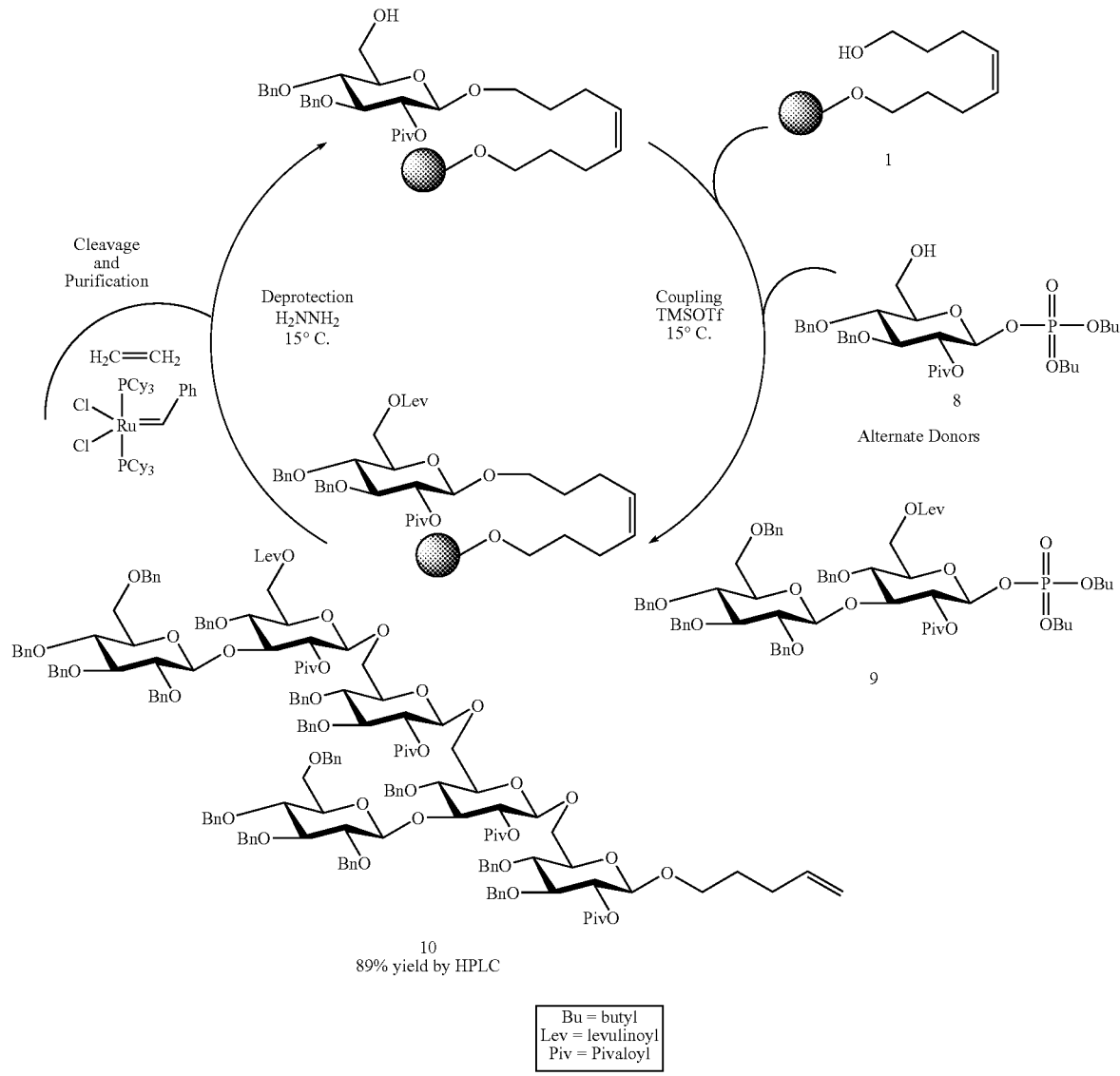

Glycosylation Conditions: 25 µmol scale: 25 µmol resin (83 mg, 0.30 mmol/g loading); 5 Eq. Donor 8 or 9 (90 and 170 mg respectively); 5Eq. TMSOTf (1 mL, 0.125 M TMSOTf in CH$_2$Cl$_2$) repeated two times for 15 min each at -15° C. Deprotection Conditions: 25 µmol scale: 4 mL, 0.25 M N$_2$H$_2$ in Pyridine:Acetic acid (3:2) repeated two times for 15 min each at 15° C.

EXAMPLE 4

Complex-Type Trisaccharide

After developing procedures for the activation and coupling of anomeric trichloroacetimidate and glycosyl phosphate donors as well as for the deprotection of acetyl and levulinoyl esters, we designed a synthesis utilizing all aspects of our automated chemistry. We chose trisaccharide 24, composed of three different monomer units, as a target structure and devised a synthesis to incorporate different donors and temporary protecting groups (Scheme 5). Glycans containing this trisaccharide motif are difficult to prepare synthetically due to the presence of Gal-β-(1→4)-GlcNAc and GlcNAc-β-(1→2)-Man linkages.

Scheme 5 Synthesis of trisaccharide 24 using glycosyl trichloroacetimidates and glycosyl phosphates

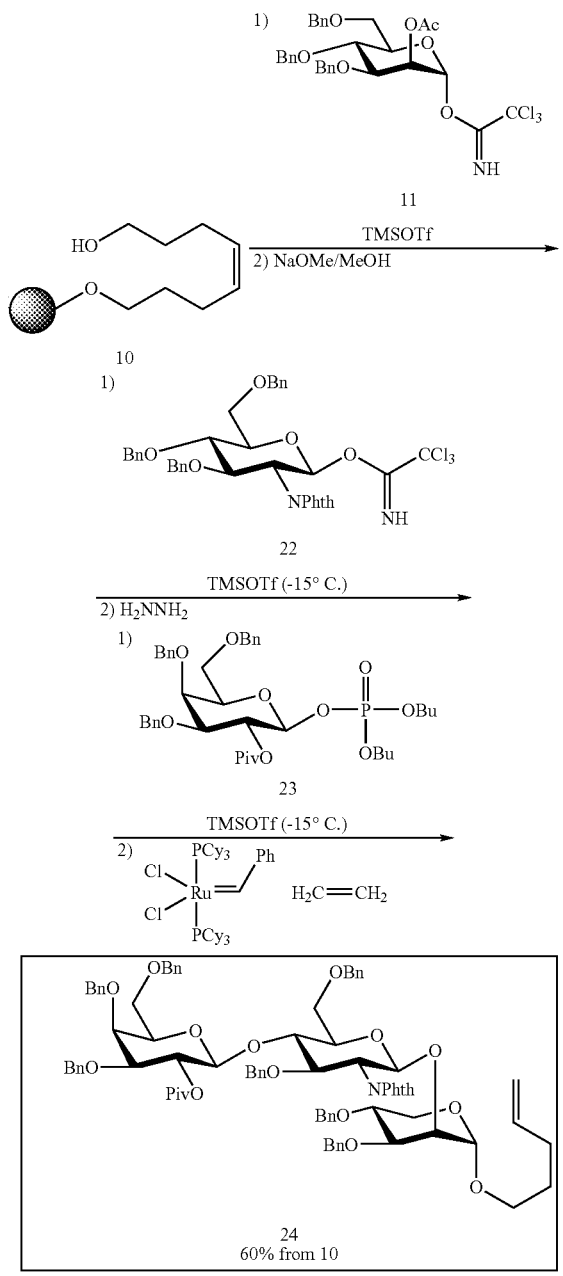

applied to other sequences. It is anticipated that each degree of orthogonality developed for our automated protocol will enhance the speed and efficiency with which increasingly complex carbohydrates can be prepared.

TABLE 4

Cycle used for the synthesis of trisaccharide 24

| STEP | FUNCTION | REAGENT | Time (min) |
|---|---|---|---|
| 1 | Couple | 4 Eq. Donor 11 and 0.4 Eq. TMSOTf | 30 |
| 2 | Wash | Dichloromethane | 6 |
| 3 | Couple | 4 Eq. Donor 11 and 0.4 Eq. TMSOTf | 30 |
| 4 | Wash | Dichloromethane | 6 |
| 5 | Wash | 1:9 Methanol:Dichloromethane | 4 |
| 6 | Deprotection | 2 × 10 Eq. NaOMe (1:9 Methanol:Dichloromethane) | 80 |
| 7 | Wash | 1:9 Methanol:Dichloromethane | 4 |
| 8 | Wash | 0.2 M Acetic Acid in Tetrahydrofuran | 4 |
| 9 | Wash | Tetrahydrofuran | 4 |
| 10 | Wash | Dichloromethane | 6 |
| 11 | Couple | 4 Eq. Donor 22 and 0.4 Eq. TMSOTf | 30 |
| 12 | Wash | Dichloromethane | 6 |
| 13 | Couple | 4 Eq. Donor 22 and 0.4 Eq. TMSOTf | 30 |
| 14 | Wash | Dichloromethane | 6 |
| 15 | Wash | 1:9 Methanol:Dichloromethane | 4 |
| 16 | Wash | Tetrahydrofuran | 4 |
| 17 | Wash | 3:2 Pyridine:Acetic Acid | 3 |
| 18 | Deprotection | 2 × 20 Eq. Hydrazine (3:2 Pyridine:Acetic Acid) | 30 |
| 19 | Wash | 3:2 Pyridine:Acetic Acid | 3 |
| 20 | Wash | 1:9 Methanol:Dichloromethane | 4 |
| 21 | Wash | 0.2 M Acetic Acid in Tetrahydrofuran | 4 |
| 22 | Wash | Tetrahydrofuran | 4 |
| 23 | Wash | Dichloromethane | 6 |
| 24 | Couple | 5 Eq. 23 Donor and 5 Eq. TMSOTf | 15 |
| 25 | Wash | Dichloromethane | 6 |
| 26 | Couple | 5 Eq. 23 Donor and 5 Eq. TMSOTf | 15 |
| 27 | Wash | 1:9 Methanol:Dichloromethane | 4 |
| 28 | Wash | Tetrahydrofuran | 4 |
| 29 | Wash | Dichloromethane | 6 |

Taking into consideration the activation and deprotection conditions necessary for the use of donors 11, 22 and 23, we devised a suitable coupling cycle (Table 4). Employing the sequence outlined in Table 4, we performed the synthesis of trisaccharide 24 on a 1% crosslinked polystyrene support (Scheme 5). After the 10 h coupling cycle, trisaccharide 24 was cleaved from the support and analyzed by HPLC to afford 24 in 60% overall yield. We were encouraged by this result as it was the first example incorporating all of the automated protocols into a single coupling cycle. Furthermore, the successful deprotection of a levulinate ester in the presence of aq phthaloyl amine protecting group provided an orthogonal protecting group strategy that can be generally applied to other sequences. It is anticipated that each degree of orthogonality developed for our automated protocol will enhance the speed and efficiency with which increasingly complex carbohydrates can be prepared.

In sum, we report the successful synthesis of biologically relevant oligosaccharides in a fully automated fashion on a solid support. A glycosylation/deprotection cycle was developed and applied to the synthesis of a decamer of an α-(1→2) mannoside. Two phytoalexin elicitor β-glucans, hexasaccharide 10 and dodecasaccharide 7, were constructed in rapid fashion using glycosyl phosphates. We anticipate that this technology will allow for the fast and reliable procurement of synthetic oligosaccharides by a non-specialist without undue difficulty. Relief from the tedious manual labor involved in carbohydrate synthesis will facilitate access to synthetic material for biochemical studies. The ease of acquiring defined structures from a machine will impact the field of glycobiology such that we may one day be able to fully appreciate the importance of oligosaccharides and glycoconjugates in nature.

EXAMPLE 5

Synthesis and Characterization of Building Blocks 8 and 9

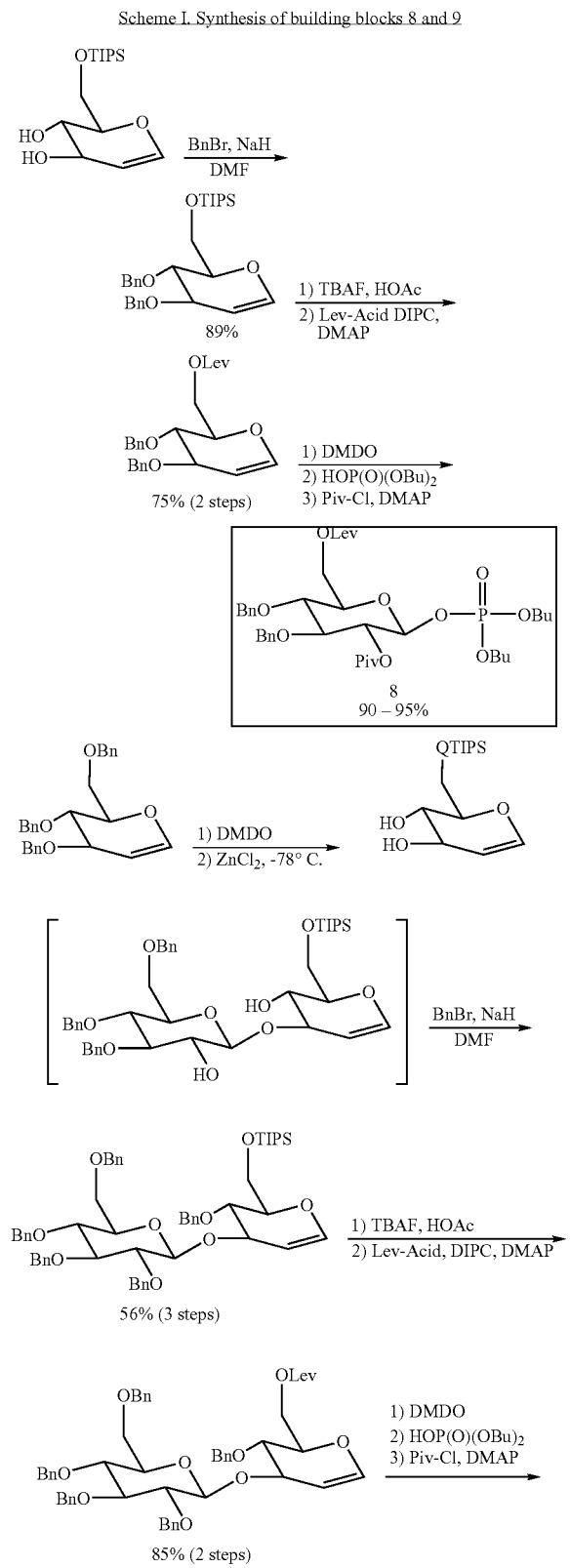

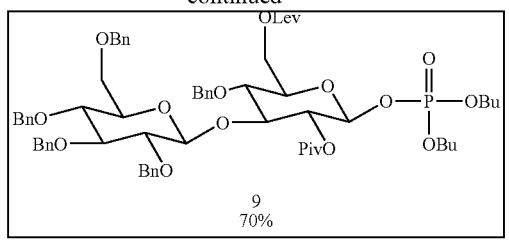

Synthesis of Dibutyl 3,4-Di-O-benzyl-6-O-Levulinoyl-2-O-pivaloyl-D-glucopyranosyl Phosphate 8.

3,4-Di-O-benzyl-6-O-levulinoyl-D-arabino-hex-1-enitol (2.12 g, 5.0 mmol) was dissolved in $CH_2Cl_2$ (5 mL) and cooled to 0° C. A 0.08 M solution of dimethyldioxirane in acetone (75 mL, 6.0 mmol) was added and the reaction mixture was stirred for 15 min. After the solvent was removed in a stream of $N_2$ and the remaining residue dried in vacuo for 15 min at 0° C., 20 mL $CH_2Cl_2$ were added. The solution was cooled to −78° C. for 15 min and dibutylphosphate (1.04 mL, 5.25 mmol) was then added dropwise over 5 min. After complete addition, the reaction mixture was warmed to 0° C. and DMAP (2.44 g, 20.0 mmol) and pivaloyl chloride (1.23 mL, 10.0 mmol) were added. The solution was warmed to room temperature over 1 h. The solvent was removed in vacuo and the residue was purified by flash column chromatography on silica gel to afford 3.29 g (90%) of 8 as a colorless oil. $^1$H NMR (500 MHz) δ 7.34–7.24 (m, 10H), 5.23 (app t, J=7.6, 7.9 Hz, 1H), 5.14 (app t, J=7.9, 9.2 Hz, 1H), 4.81 –4.78 (m, 2H), 4.72 (d, J=11.0 Hz, 1H), 4.57 (d, J=10.7 Hz, 1H), 4.39 (d, J=11.3 Hz, 1H), 4.23 (dd, J=4.0, 12.2 Hz, 1H), 3.67–3.66 (m, 2H), 2.76–2.70 (m, 2H), 2.57–2.54 (m, 2H), 2.19 (s, 3H), 1.67–1.60 (m, 4H), 1.41–1.35 (m, 4H), 1.20 (s, 9H), 0.96–0.90 (m, 6H); $^{13}$C NMR (125 MHz) δ 206.4, 177.0, 172.5, 137.9, 137.5, 128.7, 128.6, 128.4, 128.3, 128.2, 128.0, 127.5, 96.6, 96.6, 82.9, 75.3, 75.2, 73.8, 72.9, 68.2, 68.2, 68.0, 68.0, 62.7, 39.0, 38.0, 32.3, 32.3, 32.3, 32.2, 30.0, 27.9, 27.3, 18.8, 18.8, 13.8, 13.7; $^{31}$P NMR (120 MHz) δ-1.66.

Synthesis of phosphcte (2,3,4,6-tetra-O-benzyl-β-D-glucopyranosyl)-(1→3)-4-O-benzyl-6-O-levulinoyl-2-O-pivaloyl-β-D-glucopyranosyl Phosphate 9.

2,3,4,6-tetra-O-benzyl-β-D-glucopyranosyl-(1→3)-4-O-benzyl-6-O-levulinoyl-D-arabino-hex-1-enitol (1.00 g, 1.14 mmol) was dissolved in $CH_2Cl_2$ (5 mL) and cooled to 0° C. A 0.08 M solution of dimethyldioxirane in acetone (25 mL, 1.77 mmol) was added and the reaction mixture was stirred for 15 min. After the solvent was removed in a stream of $N_2$ and the remaining residue dried in vacuo for 15 min at 0° C., 20 mL $CH_2Cl_2$ were added. The solution was cooled to −78° C. for 15 min and dibutylphosphate (0.26 mL, 1.30 mmol) was then added dropwise over 5 min. After complete addition, the reaction mixture was warmed to 0° C. and DMAP (0.57 g, 4.72 mmol) and pivaloyl chloride (0.29 mL, 2.36 mmol) were added. The solution was warmed to room temperature over 1 h. The solvent was removed in vacuo and the residue was purified by flash column chromatography on silica gel to afford 950 mg (70%) of 9 as a colorless oil. $^1$H NMR (500 MHz) δ7.32–7.24 (m, 25H), 5.22 (app t, J=7.9, 9.4 Hz, 1H), 5.14 (app t, J=6.4, 7.9 Hz, 1H), 5.01 (d, J=11.0 Hz, 1H), 4.93 (d, J=11.6 Hz, 1H), 4.87 (d, J=11.0 Hz, 1H), 4.81 (d, J=10.7 Hz, 1H), 4.74 (d, J=11.0 Hz, 1H), 4.67 (d, J=7.9 Hz, 1H), 4.64–4.54 (m, 3H), 4.48 (s, 2H), 4.38–4.36 (m, 1H), 4.23 (dd, J=4.3, 11.9 Hz, 1H), 4.18–4.11 (m, 2H), 4.07–3.98 (m, 4H), 3.80 (d, J=11.0 Hz, 1H), 3.64–3.54 (m, 4H), 2.20 (s, 3H), 1.63–1.61 (m, 4H), 1.40–1.35 (m, 4H), 1.23 (s, 9H), 0.95–0.90 (m, 6H); $^{13}$C NMR (125 MHz) δ 206.5, 176.6, 172.5, 171.4, 138.6, 138.5, 138.1, 129.0, 128.9, 128.8, 128.6, 128.5, 128.5, 128.3, 128.3, 128.1, 128.0, 127.7, 127.7, 127.6, 103.5, 96.5, 96.5, 84.8, 82.6, 9.2, 78.2, 75.9, 75.4, 75.2, 75.1, 75.0, 73.8, 73.6, 73.6, 73.2, 73.1, 69.3, 68.3, 68.2, 68.0, 67.9, 62.9, 60.6, 39.0, 38.0, 32.3, 32.3, 32.3, 30.0, 27.9, 27.5, 27.4, 27.3, 21.3, 18.8, 18.8, 14.4, 13.8, 13.8; $^{31}$P NMR (120 MHz) δ-2.33.

EXAMPLE 6

Evaluation of Optimal Temperature for Phosphate Glycosylations

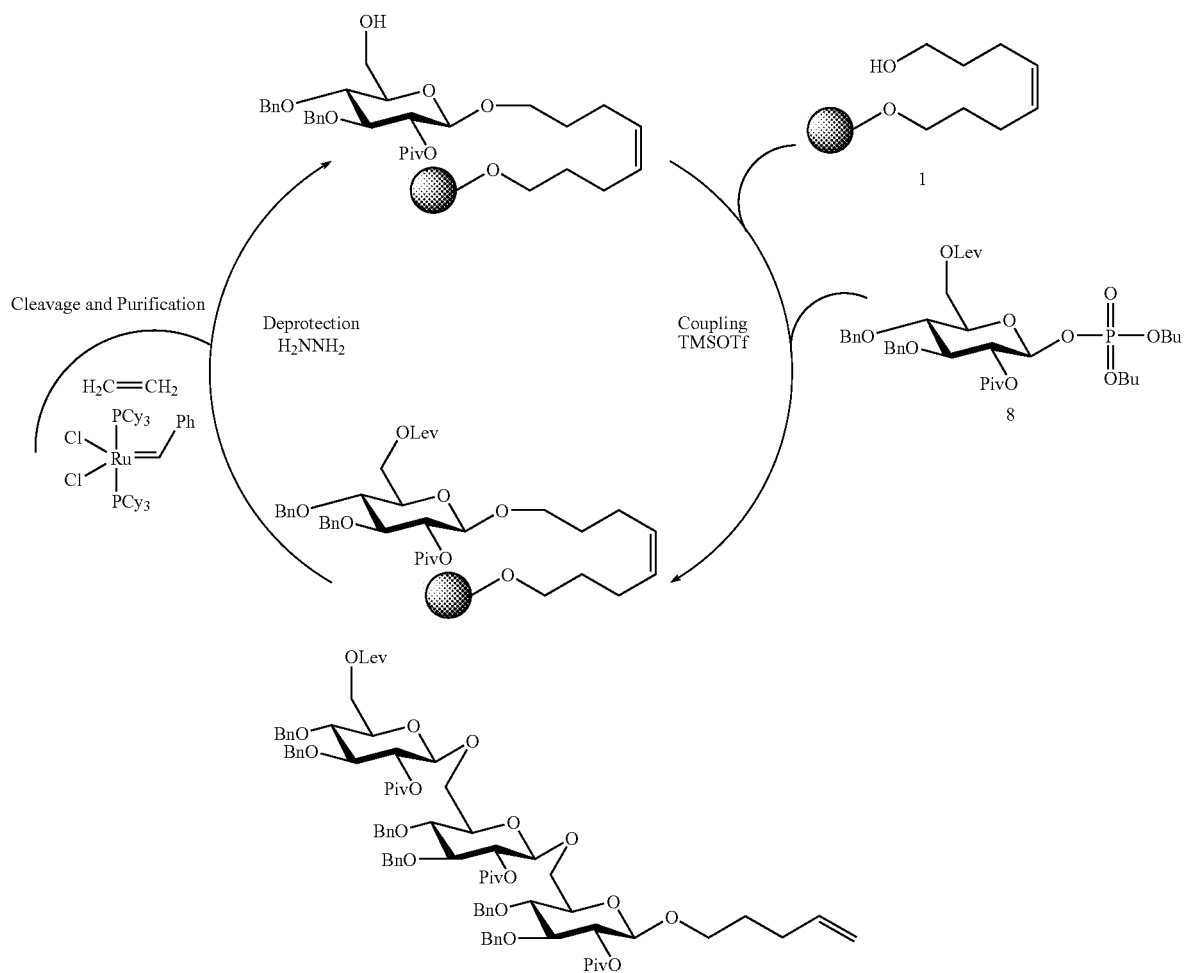

Figure 6:
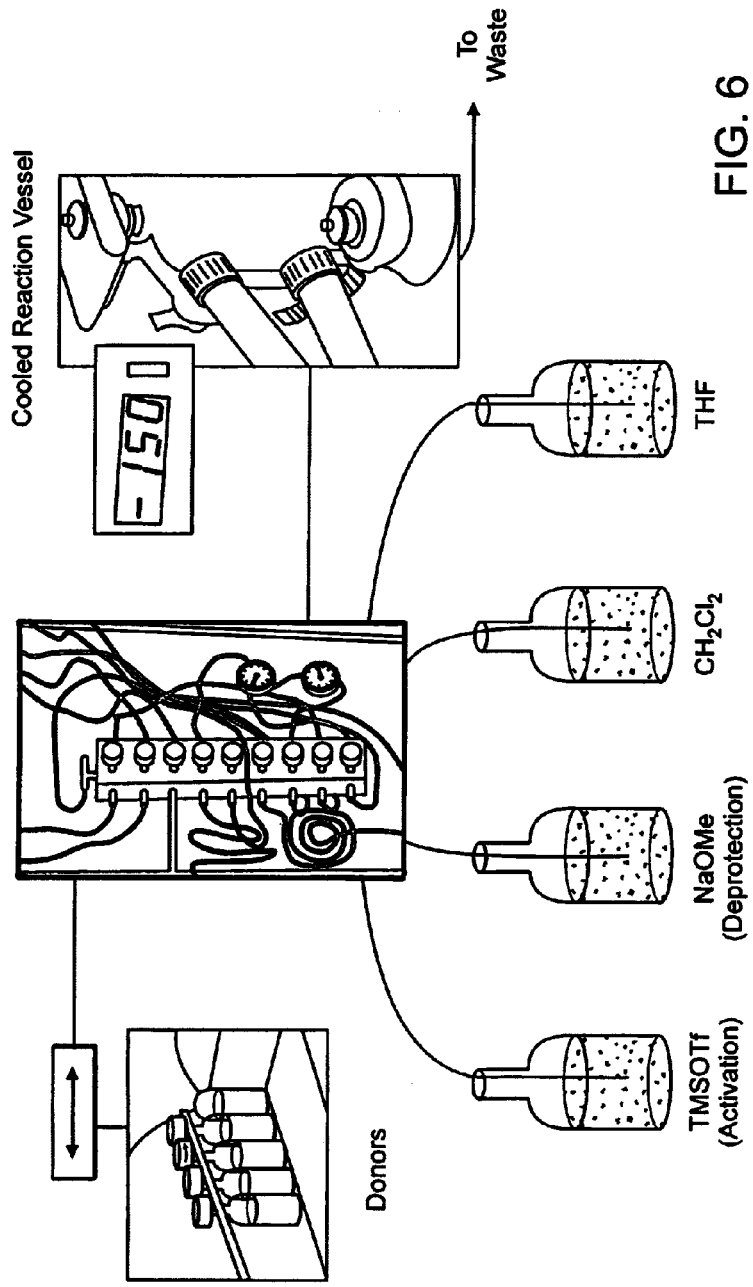
FIG. 6 depicts another embodiment of an automated oligosaccharide synthesizer in accordance with the present invention.

Trisaccharide synthesis was carried out at room temperature and at -15° C. using the following conditions. 25 μmol scale:25 μmol resin (83 mg, 0.30 mmol/g loading); 5 Eq. donor8 (90 mg); 5 Eq. TMSOTf (1 Ml, 0.125 M TMSOTf in CH$_2$Cl$_2$) for 15 min. Deprotection conditoions: 25 μmol scale: 4mL, 0.25 M N$_2$H$_4$ in pyridine:acetic acid (3:2). HPLC analysis of cleaved products from the room temperature synthesis and the -15° C. synthesis are shown in Figure 5 and Figure 6 respectively.

HPLC data for trimer synthesis using phosphate 8 at room temperature (Scheme II):
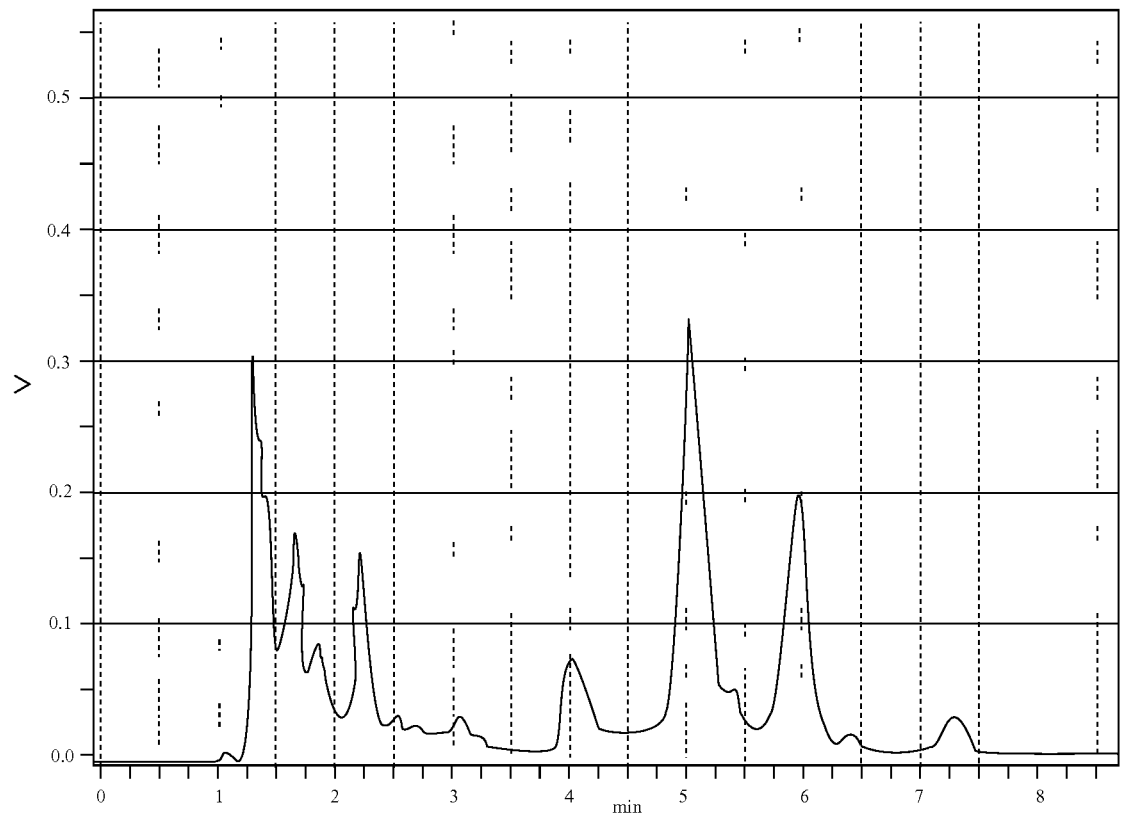
Analytical HPLC chromatogram of room temperature triglucoside synthesis following resin cleavage. Flow rate = 1 mL/min, 20 → 30% EtOAc/Hexanes (20 min): 5 min = trimer
HPLC data for trimer synthesis using phosphate 8 at -15° C. (Scheme II):

-continued

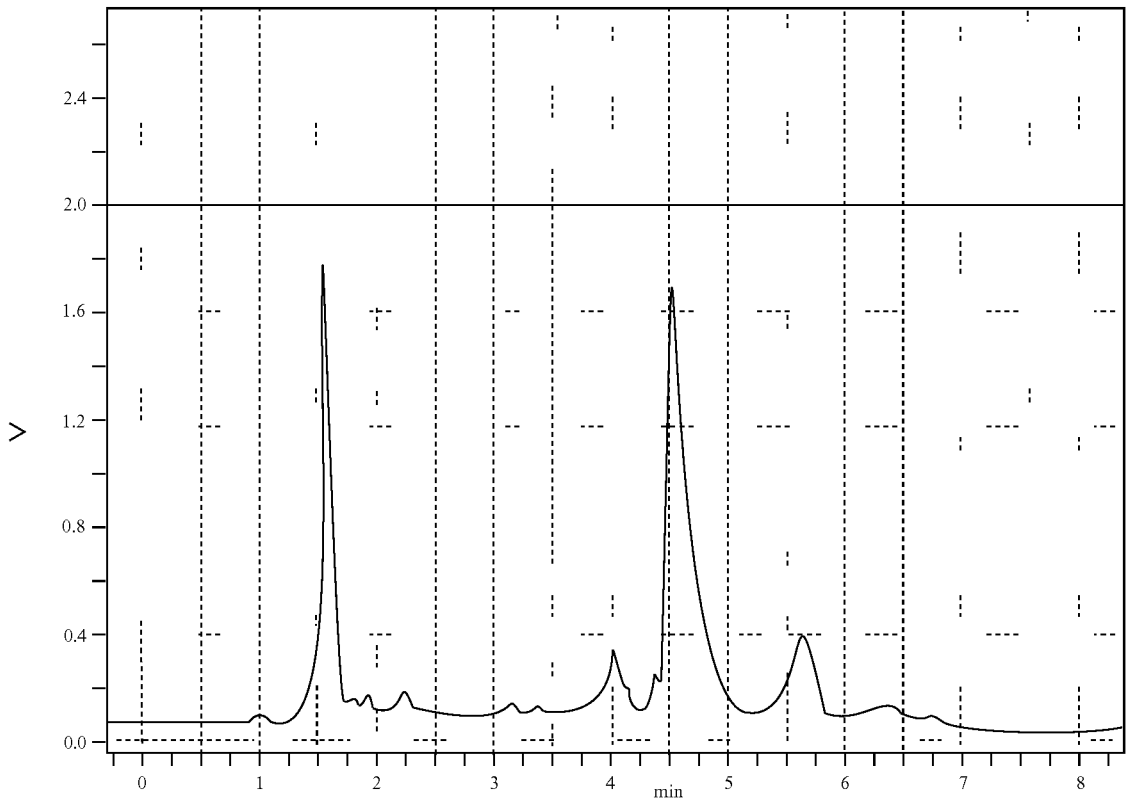

Analytical HPLC chromatogram of -15° C. triglucoside synthesis following resin cleavage. Flow rate = 1 mL/min, 20 ⟶ 30% EtOAc/Hexanes (20 min): 5 min = trimer Incorporation by Reference All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An apparatus for the automated solid-phase synthesis of oligosaccharides, comprising:
    a reaction vessel containing at least one insoluble resin bead, wherein the at least one insoluble resin bead is comprised of an octenediol functionalized resin;
    at least one donor vessel containing a saccharide donor solution;
    at least one activator vessel containing an activating reagent solution;
    at least one deblocking vessel containing a deblocking reagent solution;
    at least one solvent vessel containing a solvent;
    a solution transfer system capable of transferring the saccharide donor solution, activating reagent solution, deblocking reagent solution, and solvent to the reaction vessel; and
    a computer for controlling the solution transfer system.

2. The apparatus of claim 1, wherein a glycosyl acceptor is tethered to the resin bead via the octenediol.

3. The apparatus of claim 1, further comprising a temperature control unit for regulating the temperature of the reaction vessel.

4. The apparatus of claim 3, wherein the temperature control unit is controlled by the computer.

5. The apparatus of claim 3, wherein the temperature control unit measures the internal temperature of the reaction vessel.

6. The apparatus of claim 3, wherein the reaction vessel is a double-wall structure forming two cavities, wherein the first cavity accommodates the synthesis of oligosaccharides, and wherein the second cavity accommodates a coolant of the temperature control unit.

7. The apparatus of claim 6, wherein the double-wall structure of the reaction vessel is comprised of glass.

8. The apparatus of claim 3, wherein the temperature control unit is capable of maintaining the reaction vessel at a temperature of between −80° C. and +60° C.

9. The apparatus of claim 3, wherein the temperature control unit is capable of maintaining the reaction vessel at a temperature of between −25° C. and +40° C.

10. The apparatus of claim 1, wherein the at least one donor vessel contains a solution comprising a glycosyl trichloroacetimidate.

11. The apparatus of claim 1, wherein the at least one donor vessel contains a solution comprising a glycosyl phosphate.

12. The apparatus of claim 1, wherein the at least one activator vessel contains a solution comprising a Lewis acid.

13. The apparatus of claim 12, wherein the at least one activator vessel contains a solution comprising a silyl trifluoromethanesulfonate.

14. The apparatus of claim 12, wherein the at least one activator vessel contains a solution comprising trimethylsilyl trifluoromethanesulfonate.

15. The apparatus of claim 1, wherein the at least one deblocking vessel contains a solution comprising sodium methoxide.

16. The apparatus of claim 1, wherein the at least one deblocking vessel contains a solution comprising hydrazine.

17. The apparatus of claim 1, wherein the at least one solvent vessel contains dichloromethane.

18. The apparatus of claim 1, wherein the at least one solvent vessel contains tetrahydrofuran.

19. The apparatus of claim 1, wherein the at least one solvent vessel contains methanol.

20. The apparatus of claim 2, wherein the at least one donor vessel contains a solution comprising a glycosyl trichloroacetimidate, the at least one activator vessel contains a solution comprising trimethylsilyl trifluoromethanesulfonate, the at least one deblocking vessel contains a solution comprising sodium methoxide, a first solvent vessel contains dichloromethane, a second solvent vessel contains methanol, and a third solvent vessel contains tetrahydrofuran.

21. The apparatus of claim 2, wherein the at least one donor vessel contains a solution comprising a glycosyl phosphate, the at least one activator vessel contains a solution comprising trimethylsilyl trifluoromethanesulfonate, the at least one deblocking vessel contains a solution comprising sodium methoxide, a first solvent vessel contains dichloromethane, a second solvent vessel contains methanol, and a third solvent vessel contains tetrahydrofuran.

22. The apparatus of claim 1, further comprising at least one blocking vessel containing a blocking reagent solution.

23. The apparatus of claim 22, wherein the at least one blocking vessel contains a solution comprising benzyl trichloroacetimidate.

24. The apparatus of claim 22, wherein the at least one blocking vessel contains a solution comprising a carboxylic acid.

25. The apparatus of claim 24, wherein the carboxylic acid is levulinic acid.

26. The apparatus of claim 22, further comprising a temperature control unit for regulating the temperature of the reaction vessel, and wherein a glycosyl acceptor is tethered to the resin bead via the octenediol.

27. The apparatus of claim 26, wherein the at least one blocking vessel contains a solution comprising levulinic acid, the at least one donor vessel contains a solution comprising a glycosyl phosphate donor, the at least one activator vessel contains a solution comprising trimethylsilyl trifluoromethanesulfonate, the at least one deblocking vessel contains a solution comprising hydrazine, a first solvent vessel contains dichloromethane, a second solvent vessel contains methanol, and a third solvent vessel contains tetrahydrofuran, a fourth solvent vessel contains a solution comprising pyridine and acetic acid, and a fifth solvent vessel contains a 0.2 M solution of acetic acid in tetrahydrofuran.

28. The apparatus of claim 26, wherein the at least one blocking vessel contains a solution comprising levulinic acid, a first donor vessel contains a solution comprising a glycosyl trichloroacetimidate, a second donor vessel contains a solution comprising a first glycosyl phosphate, a third donor vessel contains a solution comprising a second glycosyl phosphate, the at least one activator vessel contains a solution comprising trimethylsilyl trifluoromethanesulfonate, a first deblocking vessel contains a solution comprising hydrazine, a second deblocking vessel contains a solution comprising sodium methoxide, a first solvent vessel contains dichloromethane, a second solvent vessel contains methanol, and a third solvent vessel contains tetrahydrofuran, a fourth solvent vessel contains a solution comprising pyridine and acetic acid, and a fifth solvent vessel contains a 0.2 M solution of acetic acid in tetrahydrofuran.

* * * * *